(12) United States Patent
Hiotis

(10) Patent No.: US 10,238,723 B2
(45) Date of Patent: Mar. 26, 2019

(54) AUTOLOGOUS TUMOR LYSATE-LOADED DENDRITIC CELL VACCINE FOR TREATMENT OF LIVER CANCER

(71) Applicant: Icahn School of Medicine At Mount Sinai, New York, NY (US)

(72) Inventor: Spiros P. Hiotis, New York, NY (US)

(73) Assignee: Icahn School of Medicine at Mount Sinai, New York, NY (US)

(*) Notice: Subject to any disclaimer, the term of this patent is extended or adjusted under 35 U.S.C. 154(b) by 0 days.

(21) Appl. No.: 14/775,862

(22) PCT Filed: Mar. 6, 2014

(86) PCT No.: PCT/US2014/021282
§ 371 (c)(1),
(2) Date: Sep. 14, 2015

(87) PCT Pub. No.: WO2014/149871
PCT Pub. Date: Sep. 25, 2014

(65) Prior Publication Data
US 2016/0008446 A1 Jan. 14, 2016

Related U.S. Application Data

(60) Provisional application No. 61/784,846, filed on Mar. 14, 2013, provisional application No. 61/791,732, filed on Mar. 15, 2013.

(51) Int. Cl.
| | | |
|---|---|---|
| *A61K 35/15* | (2015.01) | |
| *A61K 35/13* | (2015.01) | |
| *A61K 39/00* | (2006.01) | |
| *C12N 5/0784* | (2010.01) | |

(52) U.S. Cl.
CPC .......... *A61K 39/0011* (2013.01); *A61K 35/13* (2013.01); *A61K 35/15* (2013.01); *C12N 5/064* (2013.01); *C12N 5/0639* (2013.01); *A61K 2039/5154* (2013.01); *A61K 2039/5158* (2013.01); *A61K 2039/54* (2013.01); *A61K 2039/545* (2013.01); *C12N 2501/052* (2013.01); *C12N 2501/22* (2013.01); *C12N 2501/2304* (2013.01)

(58) Field of Classification Search
CPC ..... A61K 35/15; A61K 35/13; A61K 39/0011
USPC ............... 424/277.1; 435/325, 366
See application file for complete search history.

(56) References Cited

U.S. PATENT DOCUMENTS

| | | | |
|---|---|---|---|
| 4,814,470 A | 3/1989 | Colin et al. | |
| 4,857,653 A | 8/1989 | Colin et al. | |
| 4,924,011 A | 5/1990 | Denis et al. | |
| 5,290,957 A | 3/1994 | Correa et al. | |
| 5,292,921 A | 3/1994 | Correa et al. | |
| 5,438,072 A | 8/1995 | Bobee et al. | |
| 5,587,493 A | 12/1996 | Bouchard et al. | |
| 2006/0177420 A1 | 8/2006 | Felzmann | |
| 2007/0281352 A1 | 12/2007 | Dietz et al. | |
| 2011/0104210 A1* | 5/2011 | Black ..................... | A61K 35/15 424/277.1 |

FOREIGN PATENT DOCUMENTS

| | | | |
|---|---|---|---|
| CN | 102439137 A1 | | 3/2012 |
| CN | 102439137 | * | 5/2012 |
| EP | 0253738 | | 1/1988 |
| WO | WO 91/17976 | | 11/1991 |
| WO | WO 93/00928 | | 1/1993 |
| WO | WO 93/00929 | | 1/1993 |
| WO | WO 95/00632 | | 1/1995 |
| WO | WO 96/01815 | | 1/1996 |
| WO | WO 2006/083289 | * | 8/2006 |
| WO | WO 2011/115970 | | 9/2011 |

OTHER PUBLICATIONS

Dohnal et al., "Phase I study of tumor Ag-loaded IL-12 secreting semi-mature DC for the treatment of pediatric cancer", Cytotherapy, 2007, vol. 9, No. 8, pp. 755-770.

Lee et al., "Vaccination of Advanced Hepatocellular Carcinoma Patients with Tumor Lysate-Pulsed Dendritic Cells A Clinical Trial", Journal of Immunotherapy by Lippincott Williams & Wilkings, Inc., vol. 28, No. 5, Sep./Oct. 2005, 9 pages.

El Ansary, et al., "Immunotherapy by autologous dendritic cell vaccine in patients with advanced HCC", Journal of Cancer Research and Clinical Oncology, vol. 139, No. 1, Jan. 2013, 10 pages.

Iwashita et al., "Potent Stimuli Combined with Lipopolysaccaride and IFNgamma may improve Immunotherapy against HCC by Increasing the Maturation and Subsequent Immune Response of the Dendritic Cells", Cancer Biotherapy & Radiopharmaceuticals, vol. 18, No. 1, Feb. 2003, 8 pages.

Extended European Search Report for EP14768332.0 dated Sep. 23, 2016. 11 pages.

International Search Report for PCT/US2014/021282 dated May 23, 2014. 5 pages.

Shibolet et al., "Nkt and Cd8 Lymphocytes Mediate Suppression of Hepatocellular Carcinoma Growth Via Tumor Antigen-Pulsed Dendritic Cells", International Journal of Cancer, vol. 106, No. 2, pp. 236-243, Aug. 20, 2003.

Salio et al., "Mature Dendritic Cells Prime Functionally Superior Melan-A-Specific CD8+ Lymphocytes as Compared with Nonprofessional APC", Journal of Immunology, vol. 167, No. 3, pp. 1188.1197, Aug. 1, 2001.

(Continued)

Primary Examiner — Yan Xiao
(74) Attorney, Agent, or Firm — Fish & Richardson P.C.

(57) ABSTRACT

The present disclosure provides compositions comprising mature dendritic cells loaded with autologous tumor cell lysates for the treatment of liver cancers, such as hepatocellular carcinoma. Hepatocellular carcinoma (HCC) is the fifth leading cancer and third leading cause of cancer-related mortality worldwide. Surgical resection and liver transplantation remain the mainstay of effective therapy for patients with early disease. However, a prevalent problem with HCC is the high likelihood of initial diagnosis at an advanced stage.

10 Claims, 17 Drawing Sheets
Specification includes a Sequence Listing.

(56) References Cited

OTHER PUBLICATIONS

Lopez et al., "Prolonged Survival of Dendritic Cell-Vaccinated Melanoma Patients Correlates With Tumor-Specific Delayed Type IV Hypersensitivity Response and Reduction of Tumor Growth Factor b-Expressing T Cells", Journal of Clinical Oncology, vol. 27, No. 6, pp. 945-952, Feb. 20, 2009.

Alfaro et al., "Pilot Clinical Trial of Type 1 Dendritic Cells Loaded with Autologous Tumor Lysates Combined with GM-CSF, Pegylated IFN, and Cyclophosphamide for Metastatic Cancer Patients", Journal of Immunology, vol. 187, No. 11, pp. 6130-6142, Dec. 1, 2011.

Prasad et al., "Dendritic Cells Loaded with Stressed Tumor Cells Elicit Long-Lasting Protective Tumor Immunity in Mice Depleted of CD4+CD25+ Regulatory T Cells", Journal of Immunology, vol. 174, No. 1, pp. 90-98, Jan. 1, 2005.

Goodman, "Grading and staging systems for inflammation and fibrosis in chronic liver diseases," Journal of Hepatology, Oct. 2007, 47(4):598-607.

Iscove and Melchers, "Complete replacement of serum by albumin, transferrin, and soybean lipid in cultures of lipopolysaccharide-reactive B lymphocytes," J. Exp. Med, Mar. 1978, 147:923-933.

Kokkinopoulos et al., "Toll-like receptor mRNA expression patterns in human dendritic cells and monocytes," Molecular Immunology, May 2005, 42: 957-968.

Phuphanich et al., "Phase I trial of a multi-epitope-pulsed dendritic cell vaccine for patients with newly diagnosed glioblastoma," Cancer Immunol Immunother, Jan. 2013, 62(1):125-3.

Stachi-Fainaro et al., "Inhibition of vessel permeability by TNP-470 and its polymer conjugate, caplostatin," Cancer Cell, Mar. 2005, 7(3): 251-261.

Summons to Attend Oral Proceedings in European Application No. 14768332.0, dated Oct. 5, 2018, 6 pages.

* cited by examiner

AUTOLOGOUS TUMOR LYSATE-LOADED DENDRITIC CELL VACCINE FOR TREATMENT OF LIVER CANCER

TECHNICAL FIELD

This invention relates to the field of immunology and cancer immunotherapy.

REFERENCE TO SEQUENCE LISTING

Pursuant to 37 C.F.R. 1.821(c), a sequence listing is submitted herewith via EFS-Web as an ASCII compliant text file named "Sequencelisting.txt" that was created on Mar. 14, 2013, and has a size of 7,510 bytes. The content of this sequence listing (Sequencelisting.txt) is incorporated by reference in its entirety.

BACKGROUND

Hepatocellular carcinoma (HCC) is the fifth leading cancer and third leading cause of cancer-related mortality worldwide. Surgical resection and liver transplantation remain the mainstay of effective therapy for patients with early disease. However, a prevalent problem with HCC is the high likelihood of initial diagnosis at an advanced stage. The aggressive natural history of HCC in patients with advanced disease is associated with poor outcomes, and many such patients are never eligible for treatment with curative intent. Even among the smaller subset of patients who are diagnosed within early oncologic (Milan) criteria and thus eligible for liver transplantation or surgical resection with expectation for cure, high rates of post-operative cancer recurrence and progression to advanced disease remain a difficult problem. Some treatment options available for patients who develop advanced HCC include: transarterialchemoembolization (TACE) and systemic therapy with multi-target tyrosine kinase inhibitors (Sorafenib), however treatment is usually palliative and overall survival associated with application of these modalities in patients with advanced disease is disappointingly low. Unfortunately, none of these treatments have been used with any demonstrable survival benefit in the adjuvant setting. Other non-surgical treatment options for advanced HCC are either ineffective or investigational. Systemic chemotherapy does not prolong survival in HCC, but has instead been found in some studies to decrease survival. Thus a demand for novel non-surgical treatments persists in the clinical management of advanced HCC, and strategies utilizing optimized immunotherapy are needed.

SUMMARY

The present disclosure is based at least in part on the discovery herein that: (1) expression of FoxP3 in hepatitis B virus (HBV)-associated hepatocellular carcinoma (HCC) tumors is associated with mortality in humans and, (2) the compositions described herein, which comprises LPS-matured tumor lysate loaded dendritic cells (DCs), selectively reduce the number of FoxP3+T regulatory cells (Tregs) in liver tumors and are highly effective for treating liver cancer.

Thus, in certain aspects, a composition is provided that comprises: (a) DCs (i) autologous to a subject with a liver tumor, (ii) matured in the presence of LPS and, (iii) loaded with tumor cell lysate prepared from liver tumor cells obtained from the subject; and (b) the property of selectively reducing Tregs in the liver tumor when administered to the subject. In other aspects, a composition for treating a liver tumor in a subject is provided, wherein the composition is prepared by a method comprising: (a) loading DCs autologous to the subject with a tumor cell lysate prepared by repeated freeze-thaw cycles of tumor cells obtained from the subject; and (b) incubating the DCs in the presence of LPS to mature the DCs; which composition selectively reduces Tregs in the subject's liver tumor when administered to the subject. In some aspects, step (a) is performed before step (b). In other aspects, step (b) is performed before step (a). Preferably, the above-described compositions are immunogenic compositions. In certain aspects, the immunogenic composition is a vaccine. In some aspects, loading the DC comprises incubating the DCs in the presence of the tumor cell lysate. In certain aspects, the liver tumor is hepatocellular carcinoma (HCC). Preferably, the Tregs are FoxP3+. In some aspects, the DCs are prepared from peripheral blood mononuclear cells (PBMCs). In other aspects, the tumor cell lysate is prepared by performing repeated freeze-thaw cycles of the tumor cells. In certain aspects, the LPS is present at a concentration of 1 µg/ml. In other aspects, the composition comprises $1 \times 10^7$ DCs. In still other aspects, the subject is human. Further, the tumor cells can be obtained from the subject by surgical resection, percutaneous needle biopsy, or laparoscopic tumor biopsy/excision.

In other aspects, disclosed herein is a method of preparing a DC-based immunogenic composition for the treatment of a liver tumor in a subject, which comprises: (a) loading DCs with a tumor cell lysate prepared from autologous tumor cells obtained from the subject; and (b) incubating the DCs in the presence of LPS; wherein, the immunogenic composition selectively reduces Tregs in the liver tumor when administered to the subject. Also disclosed is a method of selectively reducing the number of Tregs in a liver tumor of a subject, which comprises: (a) loading DCs with a tumor cell lysate prepared from autologous tumor cells obtained from the subject; (b) incubating the DCs in the presence of LPS; and (c) following steps (a) and (b), administering the DCs to the subject, thereby selectively reducing Tregs in the liver tumor. In yet other aspects, also described is a method of treating a liver tumor in a subject, which comprises: (a) loading DCs with a tumor cell lysate prepared from autologous tumor cells obtained from the subject; (b) incubating the DCs in the presence of LPS; and (c) following steps (a) and (b), administering the DCs to the subject, wherein the administration of the DCs selectively reduces Tregs in the liver tumor. In other aspects, also described is a method of treating a liver tumor in a subject, which comprises: (a) loading DCs autologous to the subject with a tumor cell lysate prepared by repeated freeze-thaw cycles of tumor cells obtained from the subject to obtain tumor-cell-lysate-loaded DCs; (b) incubating the DCs in the presence of LPS to obtain mature DCs; and, (c) intravenously administering the mature, tumor-cell-lysate-loaded DCs to the subject; wherein the administration of the DCs selectively reduces Tregs in the subject's liver tumor. In some aspects, the DCs are administered intravenously. In some aspects, step (a) is performed before step (b). In other aspects, step (b) is performed before step (a).

In the above methods, loading the DC can comprise incubating the DCs in the presence of the tumor cell lysate. Further, in some aspects, the subject has HCC. Typically, the Tregs are FoxP3+. In some aspects, the DCs are prepared from PBMCs. In certain aspects, the tumor cell lysate is prepared by performing repeated freeze-thaw cycles of the tumor cells. In some aspects, LPS is present at a concentration of 1 µg/ml. In certain aspects, the DCs are autologous to the subject. In some aspects, the subject is human. The tumor cells may be obtained from the subject by surgical resection, percutaneous needle biopsy, or laparoscopic tumor biopsy/excision. In some aspects, the above-described methods further comprise formulating the DCs for administration to the subject. In other aspects of the above methods, the PBMCs are cultured in the presence of GM-CSF and, optionally, IL-4. In still other aspects, the PBMCs are cultured in the presence of GM-CSF and IL-4.

Definitions

The following definitions are provided for clarity and illustrative purposes only, and are not intended to limit the scope of the invention.

As used herein, a cell that is "autologous" to a subject means the cell was isolated from the subject or derived from a cell that was isolated from the subject.

As used herein a DC that is "matured," e.g., in the presence of LPS or other maturing agent, or a "mature DC" expresses one or more markers selected from CD80, CD83 and CD86 on its cell surface. A human DC preferably expresses CD83 and does not express CD14.

As used herein, the term "loading," e.g., in the context of loading a DC with an antigen or antigens (e.g., tumor cell lysate), means contacting the DC with the antigen(s) under conditions sufficient to allow the DC to take up (e.g., phagocytose) the antigen(s) and/or express the antigen(s) or peptides derived from the antigen(s) in the context of MHC molecules on the DC cell surface. Thus, as used herein, a "DC loaded with tumor cell lysate" has been contacted with the tumor cell lysate under conditions that allow the DC to present peptides derived from the tumor cell lysate in the context of MHC molecules on the cell surface.

As used herein, the term "selectively reducing" a cell type, e.g., in the context of selectively reducing T regulatory cells in a liver tumor upon administration of a DC-based composition described herein, means that the administration results a decrease in the absolute number of Tregs in the liver tumor and/or the percent (%) of the Tregs relative to the total number of tumor infiltrating lymphocytes in the tumor.

As used herein, an "immunogenic composition" is a composition which is capable of stimulating an immune response to one or more antigens in the composition when administered to a subject. A non-limiting example of an immunogenic composition described herein is a vaccine (e.g., a DC-based vaccine), e.g., for the treatment of liver cancer.

As used herein "repeated freeze-thaw cycles" of isolated tumor cells means that the isolated tumor cells are frozen and thawed at least twice.

Generally, "treating" or "treatment" of a state, disorder or condition includes: (1) preventing or delaying the appearance of clinical or sub-clinical symptoms of the state, disorder or condition developing in a mammal that may be afflicted with or predisposed to the state, disorder or condition but does not yet experience or display clinical or subclinical symptoms of the state, disorder or condition; or (2) inhibiting the state, disorder or condition, i.e., arresting, reducing or delaying the development of the disease or a relapse thereof (in case of maintenance treatment) or at least one clinical or sub-clinical symptom thereof; or (3) relieving the disease, i.e., causing regression of the state, disorder or condition or at least one of its clinical or sub-clinical symptoms. The benefit to a subject to be treated is either statistically significant or at least perceptible to the patient or to the physician.

As used herein, the term "treating cancer" or "treating a tumor" (e.g., treating a liver tumor) means causing a partial or complete decrease in the rate of growth of a tumor, and/or in the size of the tumor and/or in the rate of local or distant tumor metastasis in the presence of a composition disclosed herein, and/or any decrease in tumor cell survival, and can also include a reduction in the rate of cancer recurrence, an increase in the patient's survival, and/or an increase in the patient's progression-free survival rate following treatment. The benefit to a subject to be treated is either statistically significant or at least perceptible to the patient or to the physician.

As used herein, the term "preventing" in the context of preventing a tumor or cancer (e.g., preventing liver cancer) or preventing the recurrence of a tumor or cancer in a subject means for example, to stop the development of one or more symptoms of a disease in a subject before they occur (or reoccur) or are detectable, e.g., by the patient or the patient's doctor. Preferably, the disease (e.g., cancer) does not develop at all, i.e., no symptoms of the disease are detectable. However, it can also result in delaying or slowing of the development of one or more symptoms of the disease. Alternatively, or in addition, it can result in the decreasing of the severity of one or more subsequently developed symptoms.

As used herein, the phrase "pharmaceutically acceptable" refers to molecular entities and compositions that are generally believed to be physiologically tolerable and do not typically produce an allergic or similar untoward reaction, such as gastric upset, dizziness and the like, when administered to a human. The term "pharmaceutically acceptable derivative" as used herein means any pharmaceutically acceptable salt, solvate or prodrug, e.g. ester, of a compound of the invention, which upon administration to the recipient is capable of providing (directly or indirectly) a compound of the invention, or an active metabolite or residue thereof. Such derivatives are recognizable to those skilled in the art, without undue experimentation. Nevertheless, reference is made to the teaching of Burger's Medicinal Chemistry and Drug Discovery, 5th Edition, Vol 1: Principles and Practice, which is incorporated herein by reference to the extent of teaching such derivatives. Preferred pharmaceutically acceptable derivatives are salts, solvates, esters, carbamates, and phosphate esters. Particularly preferred pharmaceutically acceptable derivatives are salts, solvates, and esters. Most preferred pharmaceutically acceptable derivatives are salts and esters.

A "therapeutically effective amount" means the amount of a compound (or, e.g., cells, e.g., DCs) that, when administered to a mammal for treating or preventing a state, disorder or condition, is sufficient to effect such treatment or prevention. The "therapeutically effective amount" will vary depending on the compound or cells, the disease and its severity and the age, weight, physical condition and responsiveness of the mammal to be treated.

The term "about" or "approximately" means within an acceptable range for the particular value as determined by one of ordinary skill in the art, which will depend in part on how the value is measured or determined, e.g., the limitations of the measurement system. For example, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5 fold, and more preferably within 2 fold, of a value. Unless otherwise stated, the term 'about' means within an acceptable error range for the particular value.

As used herein, the term "isolated" means that the referenced material is removed from the environment in which it is normally found. Thus, an isolated biological material can be free of cellular components, i.e., components of the cells or, in the case of an isolated cell, free of the tissue or blood, in which the material is found or produced.

As used herein, "combination therapy" means the treatment of a subject in need of treatment with a certain composition or drug in which the subject is treated or given one or more other compositions or drugs for the disease in conjunction with the first and/or in conjunction with one or more other therapies, such as, e.g., a cancer therapy such as chemotherapy, radiation therapy, and/or surgery. Such combination therapy can be sequential therapy wherein the patient is treated first with one treatment modality (e.g., drug or therapy), and then the other (e.g., drug or therapy), and so on, or all drugs and/or therapies can be administered simultaneously. In either case, these drugs and/or therapies are said to be "coadministered." It is to be understood that "coadministered" does not necessarily mean that the drugs and/or therapies are administered in a combined form (i.e., they may be administered separately or together to the same or different sites at the same or different times).

The terms "express" and "expression" mean allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein. The expression product itself, e.g., the resulting protein, may also be said to be "expressed" by the cell. An expression product can be characterized as intracellular, extracellular or secreted. The term "intracellular" means something that is inside a cell. The term "extracellular" means something that is outside a cell. A substance is "secreted" by a cell if it appears in significant measure outside the cell, from somewhere on or inside the cell.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
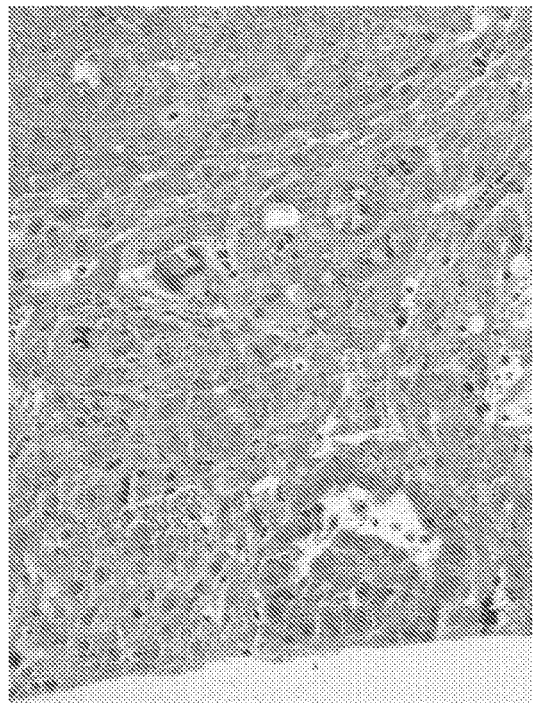
FIG. 1 contains photographs of a representative liver section taken from a mouse 3 weeks after injection of Hepa 1-6 murine hepatoma cells at a low magnification (100×, left photograph) and at a high magnification (400×, right photograph) and stained with H&E (hematoxylin and eosin). The tumor formed in this preclinical model histologically resembles poorly differentiated hepatocellular carcinoma in human.
Figure 1:
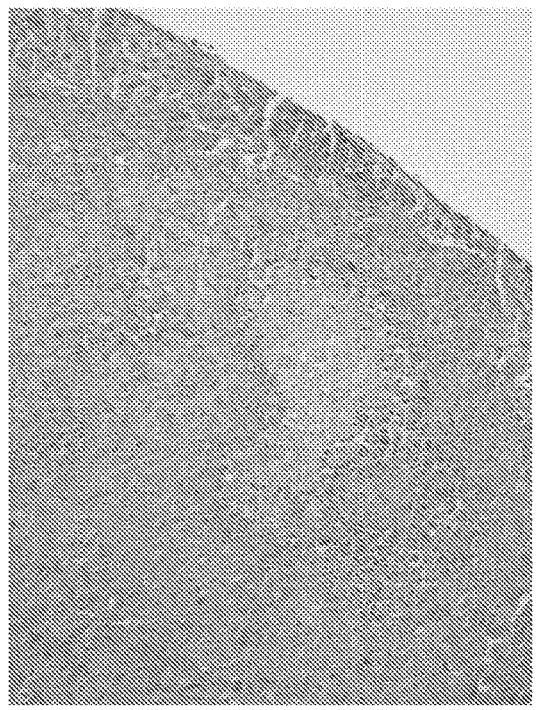

The following descriptions are provided for clarity and illustrative purposes only, and are not intended to limit the scope of the invention.

As described above, there is a need in the art for improved compositions and methods for treating liver cancer. The present disclosure describes such compositions and methods, in part by providing a dendritic cell (DC)-based immunogenic composition that reduces (e.g., selectively reduces) the number of T regulatory cells (Tregs) in liver tumors when administered to a subject with liver cancer.

In particular, as described in the Examples below, it is presently discovered that the gene FoxP3 is upregulated in human tissue obtained from hepatitis B virus (HBV)-associated HCC tumors and that FoxP3 expression in the tumors was associated with mortality. Further, in a mouse model of HCC, it is discovered that the DC-based immunogenic compositions described herein selectively reduce the number of Tregs in liver tumors and are highly effective for the treatment of liver cancers, such as HCC.

Isolation of PBMCs and Preparation of Dendritic Cell Vaccine

The present disclosure provides improved DC-based immunogenic compositions (e.g., vaccines) for treating liver cancer in a subject, for preventing the recurrence of liver cancer in a subject, and for reducing the frequency of Tregs in the liver of a subject with a liver tumor. In certain embodiments, methods of preparing a DC-based immunogenic composition for the treatment of a liver tumor in a subject are provided. The methods can include (e.g., comprise, consist essentially of, consist of): (a) loading DCs with a tumor cell lysate prepared from autologous tumor cells obtained from the subject; and (b) incubating the DCs in the presence of LPS; wherein, the immunogenic composition selectively reduces Tregs in the liver tumor when administered to the subject. Preferably, the DCs are autologous to the subject to be treated with the DC-based immunogenic composition.

For the preparation of a DC-based immunogenic composition (e.g., vaccine) for administration to humans (though the method can also be applied and/or adapted to other mammals), DCs can be prepared from peripheral blood mononuclear cells (PBMCs). Preferably the PBMCs are obtained from the subject to be treated with the composition.

PBMCs can be isolated according to any suitable method known in the art. Standard operating procedures for the collection of human PBMC are known in the art and described, e.g., in Phuphanich S, et al. Cancer Immunol Immunother. 2013 January; 62(1):125-3. An exemplary method for the isolation of PBMCs is also described, e.g., in U.S. Patent Application Publication No. 2007/0281352 by Dietz et al. See, also, e.g., Fuss et al. "Unit 7.1. Guidelines for the Collection of Mononuclear Cells (MNC) Products for the Elutra Cell Separator System Monocyte Enrichment Protocol" *Current Protocol in Immunology* (2009). Typically, blood is obtained from a subject, e.g., by collecting whole blood from the subject with a syringe into 100 IU preservative free heparin for each 10 ml of blood on a COBE spectrum apheresis system, and PBMCs are then isolated from the blood using a Ficoll gradient.

Preferably, the PBMC collection collects a product that meets the following specifications:

White Blood Cell (WBC) content: $>5 \times 10^9$ to $30 \times 10^9$;
Monocyte content: $>1 \times 10^9$;
Granulocyte content: <3%;
Red Blood Cell (RBC) content: <7.5 mL.

For the growth and culture of DCs from PBMCs, a variety of growth and culture media can be used, and the composition of such media can be readily determined by a person having ordinary skill in the art. Suitable growth media are solutions containing nutrients or metabolic additives, and include those that are serum-depleted or serum-based. Representative examples of growth media are RPMI, TC 199, Iscoves modified Dulbecco's medium [Iscove, et al., (1978) J. Exp. Med. 147:923], DMEM, Fischer's, alpha medium, NCTC, F-10, Leibovitz's L-15, MEM and McCoy's. Particular examples of nutrients that will be readily apparent to the skilled artisan include, serum albumin, transferrin, lipids, cholesterol, a reducing agent such as 2-mercaptoethanol or monothioglycerol, pyruvate, butyrate, and a glucocorticoid such as hydrocortisone 2-hemisuccinate. More particularly, the standard media includes an energy source, vitamins or other cell-supporting organic compounds, a buffer such as HEPES or Tris, which acts to stabilize the pH of the media, and various inorganic salts. Particular reference is made to PCT Publication No. WO 95/00632, wherein a variety of serum-free cellular growth media is described.

In a preferred embodiment, DCs are derived from PBMCs according to the following 8-day procedure: On Day 0, the PBMCs are thawed and plated in medium containing 1% autologous plasma onto tissue culture flasks to select for monocytes, which adhere to the plastic surface after a one hour incubation step. Lymphocytes are washed off the flasks, and the monocytes (adherent CD14+ cells) are then cultured for 5 days in the presence of granulocyte-macrophage colony-stimulating factor (GM-CSF) (with or without interleukin (IL)-4). During this period, the monocytes differentiate into immature DCs (non-adherent, CD14– CD83– cells). On Day 5, the immature DCs are harvested, washed, and transferred to 6-well plates. On Day 6, the DCs are treated with autologous tumor cell lysate (at a ratio of 5 DCs to 1 tumor cell) generated by surgical resection, percutaneous needle biopsy, or laparoscopic tumor biopsy/excision and 5 cycles of freeze/thaw cycles. One hour later, DCs are stimulated to mature by incubating with a 1 µg/ml LPS for 24 hours.

GM-CSF (with or without IL-4) induces the differentiation of monocytes (large CD14+ cells) into immature DCs (which are large, non-adherent or loosely adherent, CD14–

CD83− cells). GM-CSF is required to keep the cells alive in culture and to induce DC differentiation (whereas IL-4 may prevent monocyte differentiation into macrophages). Macrophages are easily identified as large, adherent cells with a "fried egg" appearance. Typically, 20 ng/ml GM-CSF is sufficient to induce monocyte differentiation into immature DCs (with or without 200 IU/ml IL-4). Increasing the concentration of these cytokines has no adverse effects, but tends not to improve the yield of immature DCs on Day 5. The skilled artisan will appreciate that the amount of GM-CSF (and/or IL-4) can be adjusted according to the specific culture protocol being used. GM-CSF is commercially available, e.g., from Schering-Plough, Kenilworth, N.J.), and Bayer Healthcare Pharmaceuticals. IL-4 is commercially available, e.g., from Schering Plough and Cellgenix.

While not intending to be bound by any one particular theory or mechanism of action, maturation of DCs is believed to be required because injection of antigen-loaded immature DCs into patients can result in ineffective immunization or even immune tolerance. On the final day of culture (day 7), the mature DCs (CD14− CD83+ cells) are loaded with tumor cell lysates and then washed and frozen in aliquots in a controlled-rate freezer. Quality control (QC) testing is performed afterwards, usually the following day, on frozen control aliquots. If release criteria are met, frozen aliquots designated for injection may be thawed as needed and administered to the patient.

Release criteria can include, e.g., a suitable physical appearance of the DCs. For example, by day 7 of the culture, approximately 80% of the cells in the culture should be large, non-adherent or loosely adherent cells with clearly visible cytoplasmic processes and/or veils. Most of the remaining cells will be lymphocytes (small round cells). There will be some cell debris and evidence of cell death, but this should not be a predominant feature. It is reasonable to expect a 5 to 10% yield of mature DCs (relative to the number of PBMCs plated) on day 7. In a preferred embodiment, the release criteria include >70% viable cells, negative results for all sterility and endotoxin tests, and >50% of the cells having the characteristics of mature DCs by flow cytometry (large, CD14− CD83+ cells).

Procedures for performing flow cytometry for the detection of cell marker expression are well known in the art. Fluorescently labeled anti-CD83 and anti-CD14 antibodies for detecting marker expression on DCs are available, e.g., from Abcam (Cambridge, Mass.), Caltag Laboratories (Burlingame, Calif.) and/or PharMingen (San Diego, Calif.). Other markers that can be detected using labeled antibodies include, e.g., CD45, CD86, CD40 and HLA-DR. For flow cytometry, by way of non-limiting example, cells can be washed with FACS buffer (PBS+2% fetal bovine serum, 0.1% sodium azide) and counted. One million cells in 100 μl are then added to culture tubes containing 1 μg of each labeled antibody. Cells are then incubated on ice for 40 min, washed two times with FACS buffer, and then suspended in PBS+1% paraformaldehyde and stored at 4° C. before FACS analysis.

It is presently discovered that lipopolysaccharide (LPS) (available, e.g., from Sigma-Aldrich) is particularly effective for maturing DCs for preparing the immunogenic compositions described herein. LPS is a ligand for Toll-like receptor (TLR)-4, which is expressed on mammalian DCs, including human DCs. Activation of signal transduction pathways by signaling through TLRs such as TLR4 leads to the induction of various genes including inflammatory cytokines, chemokines, major histocompatability complex, and upregulation of costimulatory molecules on DCs (i.e., leads to DC maturation). In certain embodiments, DCs are matured in the presence of 1 μg/ml LPS. However, it is to be appreciated that other concentrations of LPS may also be used to achieve comparable results (e.g., maturation of DCs, as determined, e.g., by the expression of CD83 or other maturation marker(s)). Such LPS concentrations include, without limitation, 0.001 μg/ml, 0.005 μg/ml, 0.01 μg/ml, 0.05 μg/ml, 0.1 μg/ml, 0.5 μg/ml, 1 μg/ml, 1.5 μg/ml, 2 μg/ml, 2.5 μg/ml, 3 μg/ml, 3.5 μg/ml, 4 μg/ml, 4.5 μg/ml, 5 μg/ml, 10 μg/ml, 15 μg/ml, 20 μg/ml, etc.

While LPS is the preferred agent for inducing DC maturation to prepare the immunogenic DC-based compositions described herein, the skilled artisan will appreciate that it is possible to use other maturation agents. Non-limiting examples include, e.g., other TLR-4 ligands (e.g., heat shock proteins), as well as ligands for other TLRs.

In mammalian organisms, TLRs have been shown to recognize the bacterial products LPS, lipoteichoic acid, peptidoglycan, lipoprotein, CpG-DNA, and flagellin, as well as the viral product double stranded RNA, and the yeast product zymosan. TLR2 can recognize bacterial lipoproteins, peptidoglycan, and lipoteichoic acids. TLR3 may recognize virus-derived double-stranded RNA. TLR4 is predominantly activated by lipopolysaccharide. TLR9 is required for response to unmethylated CpG DNA. TLR7 and TLR8 have been shown to recognize single stranded RNA molecules, and small synthetic antiviral molecules and TLR11 detects profilin-like protein (PLP). Furthermore, TLR5 detects bacterial flagellin. Synthetic TLR ligands, such as polyinosine-polycytidylic acid (poly(I:C)), a synthetic analog of dsRNA, is a TLR3 ligand, and is available, e.g., from InvivoGen (San Diego, Calif.).

Human DCs have been shown to express many different TLRs, depending on their maturation stage (see Kokkinopoulos et al. Molecular Immunology 42 (2005) 957-968). Thus, many of the above-described TLR ligands and/or combinations thereof may be used to induce DC maturation. Suitable concentration of TLR ligands for stimulating DC maturation are known in the art and are readily determined by one of ordinary skill in the art. In one embodiment, DCs are matured using LPS in combination with at least one other TLR ligand, e.g., such as one described above.

Typically, DCs are loaded with tumor cell lysate one hour prior to the addition of LPS to prepare the DC vaccine. In other embodiments, DCs are loaded with tumor cell lysate 0.5 hour, 1.5 hours, 2 hours, 2.5 hour, 3 hours, 3.5 hours, 4 hours, 5 hours, 6 hours, 7 hours, 8 hours, 9 hours, 10 hours, 11 hours, 12 hours, 13 hours 14 hours, 15 hours, 16 hours, 17 hours, 18 hours, 19 hours, 20 hours 21 hours, 22 hours, 23 hours, 24 hours, or longer prior to the addition of LPS. In a particularly preferred embodiment, the tumor cell lysate is autologous to the subject to be treated with the DC vaccine. It is presently discovered that DCs loaded with whole tumor cell lysate (in lieu of, e.g., only specific tumor antigens) are highly effective for reducing the frequency of Tregs in liver tumors and for treating liver cancer.

In other embodiments, DCs are loaded with tumor cell lysate one hour after the addition of LPS to prepare the DC vaccine. In other embodiments, DCs are loaded with tumor cell lysate 0.5 hour, 1.5 hours, 2 hours, 2.5 hour, 3 hours, 3.5 hours, 4 hours, 5 hours, 6 hours, 7 hours, 8 hours, 9 hours, 10 hours, 11 hours, 12 hours, 13 hours 14 hours, 15 hours, 16 hours, 17 hours, 18 hours, 19 hours, 20 hours 21 hours, 22 hours, 23 hours, 24 hours, or longer, after the addition of LPS.

In a preferred embodiment, tumor cell lysate is prepared by repeated freeze thaw cycles. For example fresh resected tumor tissues can be dissociated, digested in a protease mixture (e.g., containing HBSS, 2.5 U/ml hyaluronidase type V, 0.5 mg/ml collagenase type IV, and 0.05 mg/ml deoxyribonuclease type I) followed by filtration. After a washing step, the cells are frozen in liquid nitrogen. For thawing, the frozen cells are immersed in a 37° C. water bath for, e.g., 2 minutes (though longer or shorter times are possible). The thawed cells are then placed in liquid nitrogen to quickly freeze the cells again. This freeze/thaw cycle can be repeated at least once, twice, 3 times, 4 times, 5 times, 6 times, 7 times or more. In a preferred embodiment, the cells are frozen and thawed 5 times to prepare the tumor cell lysate. It is to be appreciate that any suitable method may be used for freeze/thawing the tumor cells.

Tumor cell lysates may also be prepared from tumor tissue according to other suitable methods known in the art, e.g., using a suitable cell lysis buffer, such as, but not limited to, NP-40 or Triton-X, or using mechanical means by a (mechanical) tissue homogenizer. Methods for preparing cell lysates are known in the art.

Typically, DCs are incubated in the presence of the tumor cell lysate (e.g. autologous tumor cell lysate) for a predetermined incubation time, e.g., 15 minutes, 20 minutes, 25 minutes, 30 minutes, 35 minutes, 40 minutes, 45 minutes, 50 minutes, 55 minutes, 1 hour, 1.5 hours, 2 hours, 2.5 hours, 3 hours, 3.5 hours or longer. In a preferred embodiment, the incubation time is 1 to 2 hours.

Typically, DCs are incubated with the tumor cell lysate at a ratio of: lysate of 1 tumor cell to 5 DCs (i.e., 1:5). The skilled artisan will appreciate that other ratios of tumor cell (lysate of tumor cell) to DC are possible, e.g., 1:1, 1:2, 1:3, 1:4, 1:6, 1:7, 1:8, 1:9, 1:10, 1:11, 1:12, 1:13, 1:14, 1:15, 1:16, 1:17, 1:18, 1:19, 1:20, etc. The effective and/or desired ratio can be readily determined by one of ordinary skill in the art.

While, in a preferred embodiment, DCs are first matured (e.g., with LPS), and then loaded with tumor cell lysate, in other embodiments of the presently disclosed compositions and methods, DCs are first loaded with tumor cell lysate and then matured (e.g., with LPS or another suitable agent).

Compositions and Formulations

While it is possible to use a composition disclosed herein (a composition comprising DCs matured with LPS and loaded with autologous tumor cell lysate) for therapy as is, it may be preferable to formulate the composition in a pharmaceutical formulation, e.g., in admixture with a suitable pharmaceutical excipient, diluent, or carrier selected with regard to the intended route of administration and standard pharmaceutical practice. Accordingly, in one aspect, the present invention provides a pharmaceutical composition or formulation comprising at least one active composition disclosed herein (e.g., the autologous DCs prepared as disclosed herein) in association with a pharmaceutically acceptable excipient, diluent, and/or carrier. The excipient, diluent and/or carrier must be "acceptable" in the sense of being compatible with the other ingredients of the formulation and not deleterious to the recipient thereof.

The compositions can be formulated for administration in any convenient way for use in human or veterinary medicine. For in vivo administration to humans, the compositions disclosed herein can be formulated according to known methods used to prepare pharmaceutically useful compositions. The DCs can be combined in admixture, either as the sole active material or with other known active materials, (e.g., one or more chemotherapeutic agents) with pharmaceutically suitable diluents (e.g., Tris-HCl, acetate, phosphate), preservatives (e.g., Thimerosal, benzyl alcohol, parabens), emulsifiers, solubilizers, adjuvants and/or carriers.

Suitable carriers and their formulations are described in Remington's Pharmaceutical Sciences, 16th ed. 1980, Mack Publishing Co.

In certain aspects, the DC-based immunogenic compositions described herein may be administered as part of a combination therapy with other active agents. While liver tumors, such as HCC, are typically relatively insensitive to systemic chemotherapy, it can be advantageous to administer such chemotherapeutic agents or other cancer therapy in combination with the DC-based immunogenic compositions described herein. Thus, non-limiting examples of chemotherapeutic agents which may be administered in a combination therapy with the compositions described herein (either in the same composition or as a separate composition), include without limitation: taxanes such as taxol, taxotere or their analogues; alkylating agents such as cyclophosphamide, isosfamide, melphalan, hexamethylmelamine, thiotepa or dacarbazine; antimetabolites such as pyrimidine analogues, for instance 5-fluorouracil, cytarabine, capecitabine, and gemcitabine or its analogues such as 2-fluorodeoxycytidine; folic acid analogues such as methotrexate, idatrexate or trimetrexate; spindle poisons including vinca alkaloids such as vinblastine, vincristine, vinorelbine and vindesine, or their synthetic analogues such as navelbine, or estramustine and a taxoid; platinum compounds such as cisplatin; epipodophyllotoxins such as etoposide or teniposide; antibiotics such as daunorubicin, doxorubicin, bleomycin or mitomycin, enzymes such as L-asparaginase, topoisomerase inhibitors such as topotecan or pyridobenzoindole derivatives; and various agents such as procarbazine, mitoxantrone, and biological response modifiers or growth factor inhibitors such as interferons or interleukins. Other chemotherapeutic agents include, though are not limited to, a p38/JAK kinase inhibitor, e.g., SB203580; a phospatidyl inositol-3 kinase (PI3K) inhibitor, e.g., LY294002; a MAPK inhibitor, e.g. PD98059; a JAK inhibitor, e.g., AG490; preferred chemotherapeutics such as UCN-01, NCS, mitomycin C (MMC), NCS, and anisomycin; taxoids in addition to those describe above (e.g., as disclosed in U.S. Pat. Nos. 4,857,653; 4,814,470; 4,924,011, 5,290,957; 5,292,921; 5,438,072; 5,587,493; European Patent No. 0 253 738; and PCT Publication Nos. WO 91/17976, WO 93/00928, WO 93/00929, and WO 96/01815. In other embodiments, a cancer therapy can include but is not limited to administration of cytokines and growth factors such as interferon (IFN)-gamma, tumor necrosis factor (TNF)-alpha, TNF-beta, and/or similar cytokines, or an antagonist of a tumor growth factor (e.g., TGF-β and IL-10). Antiangiogenic agents, include, e.g., endostatin, angiostatin, TNP-470, Caplostatin (Stachi-Fainaro et al., Cancer Cell 7(3), 251 (2005)). Drugs that interfere with intracellular protein synthesis can also be used in the methods of the present invention; such drugs are known to those skilled in the art and include puromycin, cycloheximide, and ribonuclease.

The effective amounts of compounds, compositions including pharmaceutical formulations of the present invention include doses that partially or completely achieve the desired therapeutic, prophylactic, and/or biological effect. In a specific embodiment, an effective amount of dendritic cells administered to a patient having a liver tumor is effective for reducing the size or inhibiting the growth of the liver tumor in the patient. The actual amount effective for a particular application depends on the condition being treated and the route of administration. The effective amount for use in humans can be determined from animal models. For example, a dose for humans can be formulated to achieve circulating and/or gastrointestinal concentrations that have been found to be effective in animals.

When formulated in a pharmaceutical composition or formulation, a therapeutic compound disclosed herein can be admixed with a pharmaceutically acceptable carrier or excipient. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions.

In a preferred embodiment, the DCs are formulated for administration to humans in 0.9% NaCl saline. The formulation may also contain DMSO (e.g., 10% DMSO).

Administration and Dosage

The DCs may be administered in any suitable preparation. For in vivo administration to a patient, such as a mammal, e.g., a human patient, dendritic cells of the present invention may be administered by a parenteral route. The term "parenteral" includes subcutaneous injections, intravenous, intramuscular, intracisternal injection, or infusion techniques. Also included are intra-tumoral injection, and direct intra-organ injection (e.g., intra-splenic or intra-hepatic injection). For injection or infusion techniques, the DCs may be suspended in any suitable injection buffer, such as, but not limited to PBS or PBS containing anti-coagulants.

The compositions described herein will typically contain an effective amount of DCs, alone, or in combination with an effective amount of any other active material, e.g., a chemotherapeutic agent. Effective amounts, or dosages, and desired concentrations of DCs contained in the compositions may vary depending upon many factors, including the intended use, patient's body weight and age, and route of administration.

Figure 17:
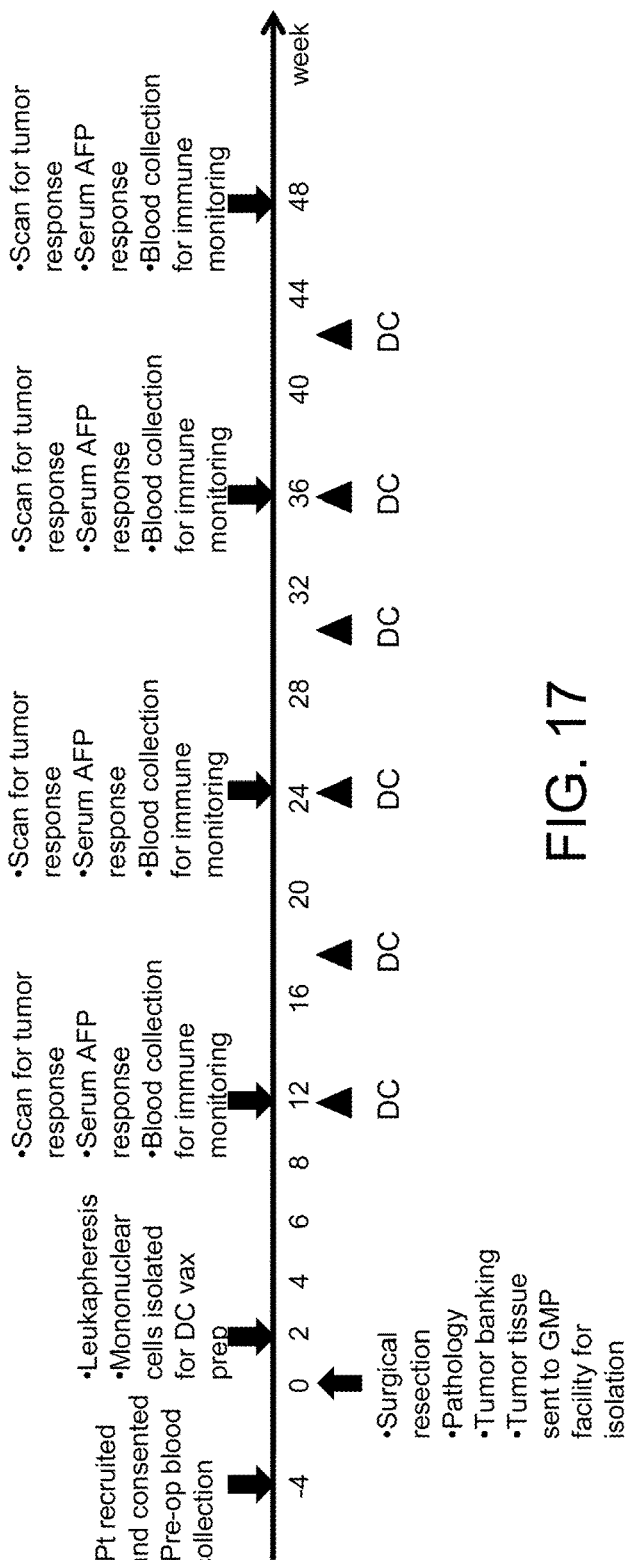
FIG. 17 is a schema summarizing the DC vaccination protocol. Arrows drawn from "DC" indicate the time point (weeks) at which the DC vaccine is administered to the patient.

The dosage of the compositions and formulations disclosed herein may vary widely, depending upon the nature of the disease, the patient's medical history, the frequency of administration, the manner of administration, the clearance of the agent from the host, and the like. The initial dose may be larger, followed by smaller maintenance doses. The dose may be administered as infrequently as weekly or biweekly, or fractionated into smaller doses and administered daily, semi-weekly, biweekly, quarterly, etc., to maintain an effective dosage level. Preliminary doses can be determined according to animal tests, and the scaling of dosages for human administration can be performed according to art-accepted practices. In certain embodiments, a subject may be administered 1 dose, 2 doses, 3 doses, 4 doses, 5 doses, 6 doses or more of a DC-based composition described herein. An exemplary dosing schedule of the DC-based immunogenic compositions described herein is illustrated in FIG. 17, in which patients receive up to six doses of the DC-based composition described in Example 2.

Keeping the above description in mind, typical dosages (effective amounts) of DCs for administration to a patient may range from $1\times10^3$ to $1\times10^8$ cells per dose, although more or less cells may be used. Preferably the number of dendritic cells ranges from $1\times10^4$ to $1\times10^8$, more preferably from $1\times10^5$ to $1\times10^8$, still more preferably from $1\times10^6$ to $1\times10^8$, and most preferably from $1\times10^6$ to $1\times10^7$. In a preferred embodiment, the DCs are administered in an amount of $1\times10^7$. However, other ranges are possible, depending on the patient's response to the treatment More-over, an initial dose may be the same as, or lower or higher than subsequently administered doses of the DCs.

The number and frequency of doses may also be determined based on the patient's response to administration of the composition, e.g., if the patient's symptoms improve and/or if the patient tolerates administration of the composition without adverse reaction; in some patients, a single dose is sufficient, other patients may receive a weekly, biweekly, or monthly administration of the DC-containing composition. The duration and frequency of treatment will depend upon the patient's response to treatment, i.e., if the patient's condition improves. For example, if the patient has a liver tumor, tumor size and/or rate of regression can be determined, e.g., by CT or MRI, or other routine methods in the art, and dosing and duration of treatment may be scaled based on the patient's individual response to treatment. Similar diagnostic tools can also be used to determine whether recurrence of a tumor has been prevented. By way of non-limiting example, response to treatment in patients with measurable disease, can be determined, e.g., by one or more of the following: the absence of tumor recurrence, absence of tumor metastasis, absence of tumor progression, increase or preservation of progression-free survival, increase or preservation of survival. Clinical response to therapy can be determined by axial imaging (e.g., computerized tomography (CT)), magnetic resonance imaging (MRI), or ultrasound, physiologic imaging (e.g., positron emission tomography (PET)), AFP levels, and/or physical examination.

Uses of the DC-Based Immunogenic Compositions

In certain aspects, the present disclosure provides methods for selectively reducing the number of Tregs in a liver tumor of a subject. In other aspects, the present disclosure describes the use of the DC-based immunogenic compositions described herein in a method and/or in a medicament for reducing the number of Tregs in a liver tumor of a subject. These methods and/or uses can include (e.g., comprises, consists essentially of, consists of): (a) loading DCs with a tumor cell lysate prepared from autologous tumor cells obtained from the subject; (b) incubating the DCs in the presence of LPS; and (c) following steps (a) and (b), administering the DCs to the subject, thereby selectively reducing Tregs in the liver tumor.

Tregs are a component of the immune system that suppress immune responses of other cells. Tregs as described herein express CD4 and Foxp3 (CD4+Foxp3+ regulatory T cells). FOXP3 is an excellent marker for Tregs, and can be detected at the mRNA and/or protein level. The nucleic acid sequence for human Foxp3 mRNA is known and has GenBank Accession No. NM_014009 (SEQ ID NO: 1). The amino acid sequence for human FOXP3 is known and has GenBank Accession No. ABQ15210 (SEQ ID NO: 2). Exemplary primer sequences that can be used to detect Foxp3 mRNA expression are forward 5'-AGAAGCAGCGTCAGTACCCCT-3' (SEQ ID NO: 3) and reverse: 5'-CTGCACGGGACTCAAGAGAC-3'(SEQ ID NO: 4). Antibodies that can be used for the detection of Tregs (e.g., CD4, FOXP3) by flow cytometry are commercially available, e.g., from Abcam.

The compositions and methods described herein may reduce the frequency of Tregs (e.g., absolute number of Tregs or percent relative to total number of tumor infiltrating lymphocytes) in the liver tumor of a subject treated with the composition by at least 0.5-fold, at least 1.5-fold, at least 2-fold, at least 2.5 fold, at least 3-fold, at least 3.5 fold, at least 4-fold, at least 5-fold, or more. In other embodiments, the compositions and methods described herein may reduce the frequency of Tregs in the liver tumor of a subject treated with the composition by at least 1%, at least 2%, at least 3%, at least 4%, at least 5%, at least 6%, at least 7%, at least 8%, at least 9%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99% or greater In other aspects, the present disclosure provides a method of treating a liver tumor in a subject. In other aspects, the present disclosure describes the use of the DC-based immunogenic compositions described herein in a method and/or in a medicament for treating a liver tumor in a subject. These methods and/or uses can include (e.g., comprise, consist essentially of, consist of): (a) loading DCs with a tumor cell lysate prepared from autologous tumor cells obtained from the subject; (b) incubating the DCs in the presence of LPS; and (c) following steps (a) and (b), administering the DCs to the subject, wherein the administration of the DCs selectively reduces Tregs in the liver tumor. In some aspects, these method and/or uses include: (a) loading DCs autologous to the subject with a tumor cell lysate prepared by repeated freeze-thaw cycles of tumor cells obtained from the subject to obtain tumor-cell-lysate-loaded DCs; (b) incubating the DCs in the presence of LPS to obtain mature DCs; and, (c) intravenously administering the mature, tumor-cell-lysate-loaded DCs to the subject; wherein the administration of the DCs selectively reduces Tregs in the subject's liver tumor.

In other aspects, the present disclosure provides a method for preventing the recurrence of liver cancer in a subject. These methods and/or uses can include (e.g., comprise, consist essentially of, consist of): (a) loading DCs with a tumor cell lysate prepared from autologous tumor cells obtained from the subject; (b) incubating the DCs in the presence of LPS; and (c) following steps (a) and (b), administering the DCs to the subject, wherein the administration of the DCs selectively reduces Tregs in the liver tumor. In some aspects, these method and/or uses include: (a) loading DCs autologous to the subject with a tumor cell lysate prepared by repeated freeze-thaw cycles of tumor cells obtained from the subject to obtain tumor-cell-lysate-loaded DCs; (b) incubating the DCs in the presence of LPS to obtain mature DCs; and, (c) intravenously administering the mature, tumor-cell-lysate-loaded DCs to the subject; wherein the administration of the DCs selectively reduces Tregs in the subject's liver tumor.

The presently disclosed methods include using autologous tumor cell lysate to prepare the DC-based immunogenic compositions. Thus, for preventing recurrence of liver cancer in a patient who does not have a liver tumor, but previously was diagnosed with a liver tumor (and treated such that the liver tumor was no longer detectable), a patient's tumor cells obtained from the patient before treatment of the liver tumor can be used to prepare the DC vaccine. The DC vaccine may then be administered to the patient to prevent recurrence of the liver tumor.

Liver cancers that may be treated using the compositions and methods disclosed herein include but are not limited to hepatocellular carcinoma (HCC) or hepatoma, cholangiocarcinoma or bile duct cancer (BDC), and other primary or secondary liver cancers. Cancers of other organs or tissues may also be treated using the compositions and methods disclosed herein, including but not limited to primary or secondary cancers of the aero-digestive tract, pharynx, esophagus, stomach, pancreas, small bowel, colon, rectum, anus, kidney, bladder, prostate, breast, ovary, uterus, bone, muscle, connective tissue, lungs, tracheal-bronchial tree, brain, ocular, skin, lymph nodes, and bone marrow.

In some embodiments, a subject with liver cancer, who is to be treated with a DC-based immunogenic composition described herein, has undergone surgical resection of the liver tumor. In other embodiments, the subject has undergone percutaneous needle biopsy, or laparoscopic tumor biopsy/excision. The patient may have undergone any suitable procedure for obtaining a tumor tissue sample for the preparation of autologous tumor cell lysate according to the methods described herein.

In some aspects, the DC-based immunogenic compositions described herein can be administered as a combination therapy. For example, a subject may either before, simultaneously, or after treatment with a DC-based immunogenic composition described herein, undergo one or more procedures or therapies, including, e.g., surgical resection, liver transplantation, cryosurgery, hepatic artery chemoembolization, percutaneous ethanol, radiofrequency ablation (RFA) (surgical and percutaneous), and/or cisplatin gel injection. As described above, in certain embodiments the DC-based immunogenic compositions may also be administered as a combination therapy with a chemotherapeutic agent.

For example, surgery can be performed in non-cirrhotic patients with hepatocellular carcinoma—and in cirrhotic patients with well-preserved synthetic functions. However, only 20% of patients are potentially resectable at the time of presentation. In noncirrhotic patients, surgical mortality is less than 3% in experienced hands, but increases to 8% in patients with cirrhosis. Not all patients are eligible for liver resection. Resection is not indicated when: 1) the tumor has spread to other parts of the liver or the body, 2) the size or location of the tumor (near major blood vessels) precludes it from being safely removed without compromising function of the remainder of the liver, 3) the associated cirrhosis or disease limits the ability to safely operate upon or remove part of the liver, and 4) other medical conditions make surgery unsafe.

RFA makes use of a "heating" probe to destroy tumors within the liver. A thin probe is placed within the tumor, typically under ultrasound guidance. After deploying the tip array, an electrical current is applied, generating heat (80-100° C.) that destroys the tumor. RFA is generally indicated for small tumors within the liver and can be applied with minimal side effects. The advantage of this technique is that it can be used either in the operating room with an open or laparoscopic approach, or directly through the skin (percutaneous approach). As with cryotherapy, RFA can be used in conjunction with liver resection. Some of the tumor may be surgically removed, while remaining disease is treated with RFA.

Hepatic artery chemoradiation is a commonly performed procedure in the treatment of unresectable liver tumors (i.e., those that are inoperable). Most hepatic tumors are supplied by the hepatic arterial system, as opposed to normal liver tissue, in which most of the blood supply comes from the portal venous system. Chemoembolization has several theoretical advantages over intravenous pump infusion therapy because it delivers highly concentrated drugs to the tumor itself and arrests blood flow, the latter prolonging contact time within the tumor. This technique deprives the tumor of its oxygen supply while achieving a drug concentration in the tumor 10-25 times greater than that which can be achieved by infusion alone. In addition, the "dwell time" for the drug is markedly prolonged, with measurable drug levels present as long as a month after chemoembolization. Up to 85% of the administered drug is trapped in the liver, minimizing systemic toxicity.

Percutaneous radio frequency ablation causes local tissue destruction by frictional heat. When the temperature surpasses 90° C., an immediate destructive effect occurs within the tumor.

Percutaneous cisplatin gel infusion is a new and promising therapeutic option for the treatment of unresectable liver tumors. Cisplatin is an anti-neoplastic drug.

In accordance with the present invention there may be employed conventional molecular biology, microbiology, protein expression and purification, antibody, and recombinant DNA techniques within the skill of the art. Such techniques are explained fully in the literature. See, e.g., Sambrook et al. (2001) *Molecular Cloning: A Laboratory Manual.* 3$^{rd}$ ed. Cold Spring Harbor Laboratory Press: Cold Spring Harbor, N.Y.; Ausubel et al. eds. (2005) *Current Protocols in Molecular Biology.* John Wiley and Sons, Inc.: Hoboken, N.J.; Bonifacino et al. eds. (2005) *Current Protocols in Cell Biology.* John Wiley and Sons, Inc.: Hoboken, N.J.; Coligan et al. eds. (2005) *Current Protocols in Immunology,* John Wiley and Sons, Inc.: Hoboken, N.J.; Coico et al. eds. (2005) *Current Protocols in Microbiology,* John Wiley and Sons, Inc.: Hoboken, N.J.; Coligan et al. eds. (2005) *Current Protocols in Protein Science,* John Wiley and Sons, Inc.: Hoboken, N.J.; and Enna et al. eds. (2005) *Current Protocols in Pharmacology,* John Wiley and Sons, Inc.: Hoboken, N.J.; *Nucleic Acid Hybridization,* Hames & Higgins eds. (1985); *Transcription And Translation,* Hames & Higgins, eds. (1984); *Animal Cell Culture* Freshney, ed. (1986); *Immobilized Cells And Enzymes,* IRL Press (1986); Perbal, *A Practical Guide To Molecular Cloning* (1984); and Harlow and Lane. *Antibodies: A Laboratory Manual* (Cold Spring Harbor Laboratory Press: 1988).

EXAMPLES

The present invention is described further below in working examples which are intended to further describe the invention without limiting the scope therein.

Example 1: Orthotopic Mouse Model of Hepatocellular Carcinoma

This Example describes the generation of a murine model for HCC based on hepatic implantation of Hepa 1-6, an AFP-expressing murine HCC cell line, in immunocompetent mice.

Materials and Methods:

1. Commercial Source of Hepa 1-6, Hepa 1-6-Luc and 3LL cells: Hepa 1-6 and 3LL cells were obtained from ATCC. Hepa 1-6-Luc cells were generated to stably express the firefly luciferase (Luc). The Luc gene was cloned into the pGL4.51 (luc2/CMV/Neo) vector. Hepa 1-6 cells were transfected, and Hepa 1-6 clones stably expressing luciferase (Hepa 1-6-Luc) were selected using G418 Sulfate. The expression of luciferase was confirmed using Luciferase Reporter Assay System (Promega).

2. Western blot: AFP was detected by Western blot using a goat anti-mouse AFP antibody (R&D Systems).

3. Bioluminescence imaging and analysis: In vivo bioluminescence imaging of luciferase-expressing Hepa 1-6 tumor was performed using a Xenogen IVIS-200 Series Imaging System (PerkinElmer, Waltham, Mass.). Imaging and measurement of bioluminescence signals were acquired and analyzed using Caliper Living Image, Version 2.50.1 (Caliper Life Sciences, Hopkinton, Mass.).

5. Administration of cyclophosphamide: Mice were treated intraperitoneally with or without cyclophosphamide (Bristol-Myers Squibb) at 200 mg/kg three days prior to tumor implantation.

Results:

An orthotopic mouse model of HCC was developed using Hepa 1-6-Luciferase ("Hepa 1-6-Luc") expressing murine hepatoma cells. $10^6$ Hepa 1-6-Luc cells were injected in a volume of 20 µl PBS into the right lobe of the liver of wild type C57L/J mice. Solid tumors developed in the mice within 3 weeks. Histology was performed and revealed that the solid tumors resembled poorly differentiated HCC in humans (FIG. 1).

Figure 2:
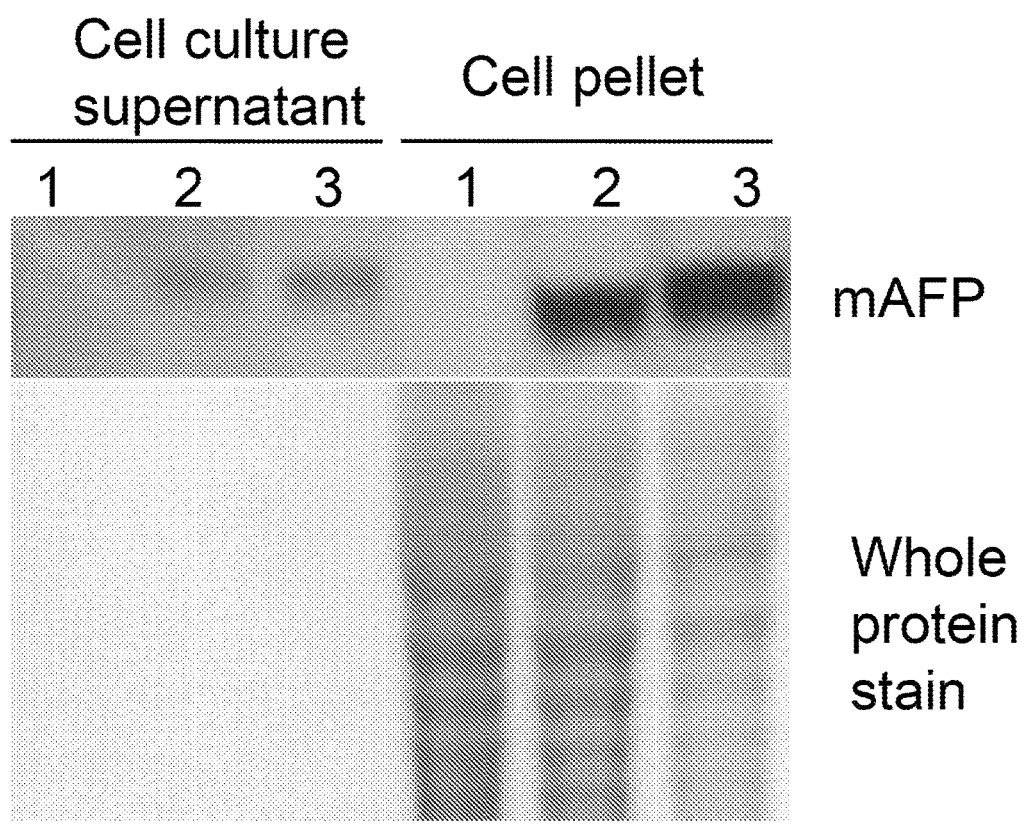
FIG. 2 is a photograph of a Western blot result detecting the expression of murine AFP (mAFP) in cell culture supernatant (leftmost lanes 1, 2 and 3) and cell pellet (rightmost lanes 1, 2 and 3). The photograph is overlaid on a photograph of the Western blot result of a whole protein stain for the same samples. Lane 1 corresponds to 3LL cells (control), lane 2 corresponds to Hepa 1-6 cells, and lane 3 corresponds to Hepa 1-6-Luciferase cells.

Alpha-fetoprotein (AFP) is a serological marker of HCC in humans. It was thus determined whether Hepa 1-6 cells secrete murine AFP. AFP levels were measured by Western blot using the antibodies described above. As shown in FIG. 2, Hepa 1-6 and Hepa 1-6-luc cells secreted AFP. 3LL cells were used as a negative control.

Figure 3A:
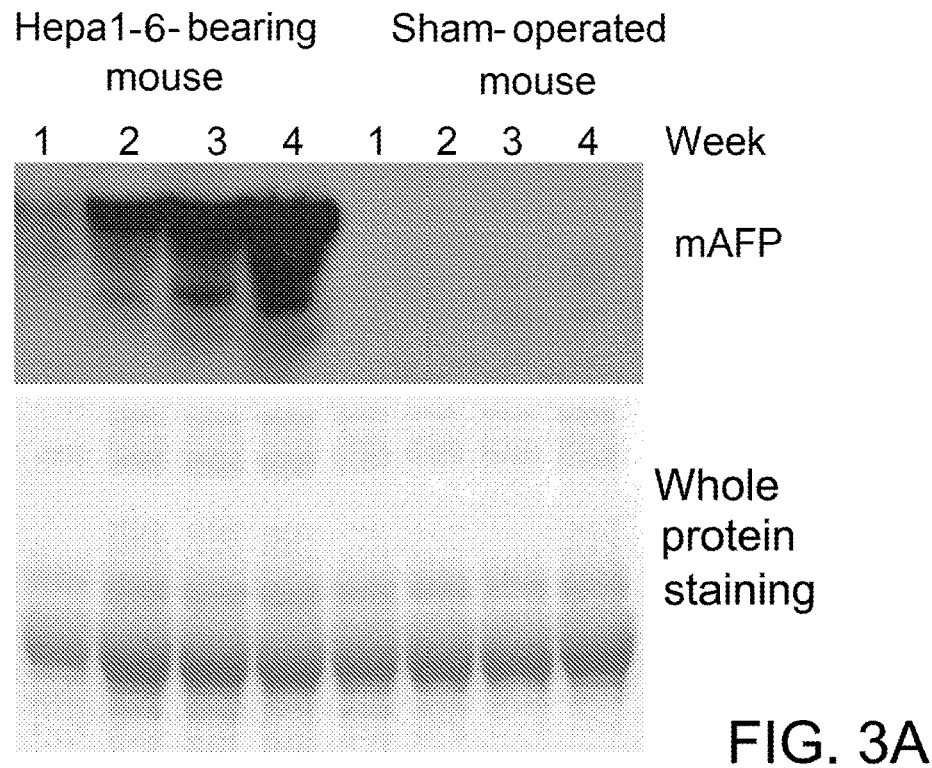
FIG. 3A is a photograph of a Western blot result for murine alpha-fetoprotein (mAFP) protein expression in plasma cells from Hepa 1-6 bearing mice (leftmost lanes 1 to 4) or from sham-operated control mice (rightmost lanes 1 to 4). The photograph is overlaid on a photograph of the Western blot result of a whole protein stain for the same samples.
Figure 3B:
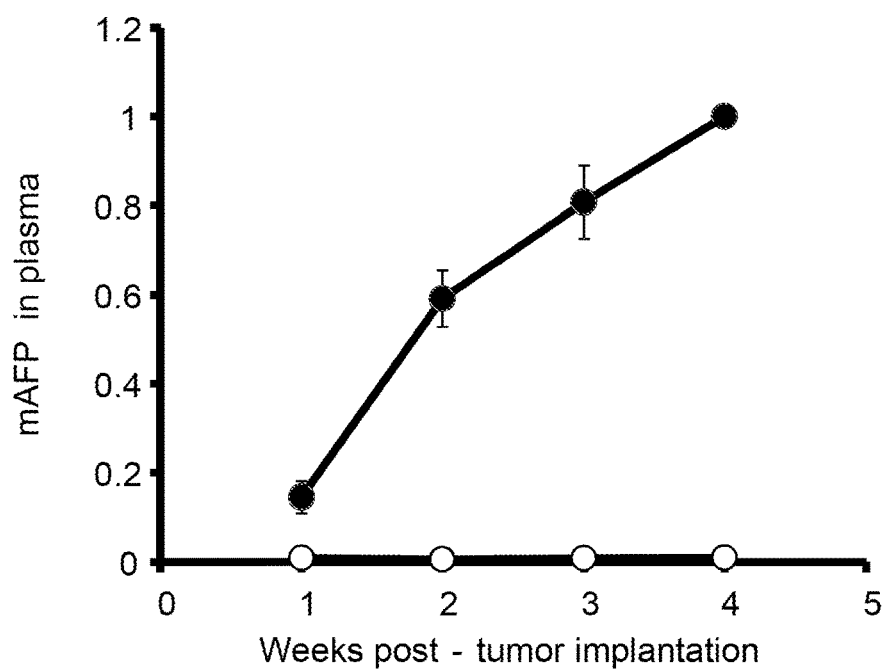
FIG. 3B is a line graph quantifying the levels of mAFP in plasma of Hepa 1-6 bearing mice or sham-operated-control mice over time (weeks post-tumor implantation).

The levels of murine AFP in vivo were also measured over the course of solid tumor development in the orthotopic mouse model. It was observed that AFP levels increased in circulation as Hepa 1-6 tumors progressed in vivo (FIG. 3A and FIG. 3B), as determined by Western blot.

Figure 4:
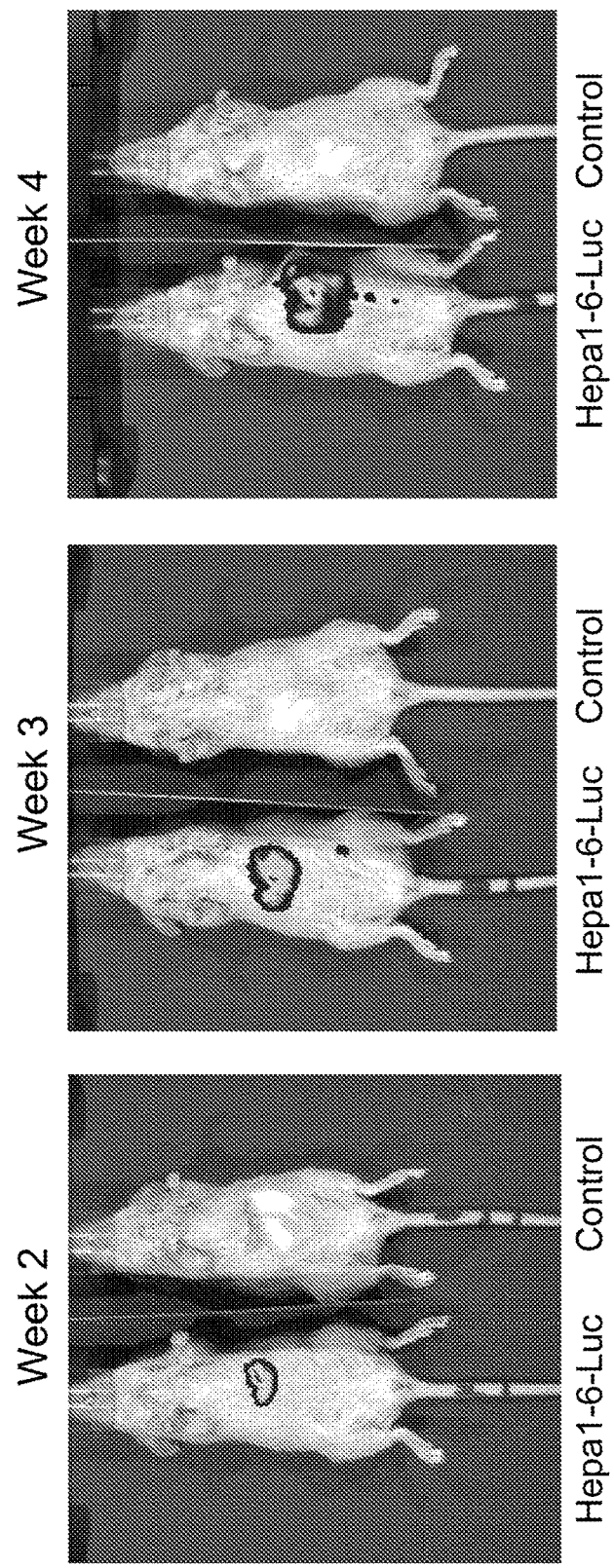
FIG. 4 contains bioluminescence images of Hepa 1-6-Luciferase ("Luc.") cell-bearing mice or sham control mice at weeks 2, 3 and 4 post-implantation of the cells.

Tumor development was monitored over time using bioluminescence imaging. As shown in FIG. 4, by week 2 the tumor was visible in the Hepa 1-6-Luc mice but not in the control, and the tumor increased in volume at 3 weeks and 4 weeks.

Figure 5:
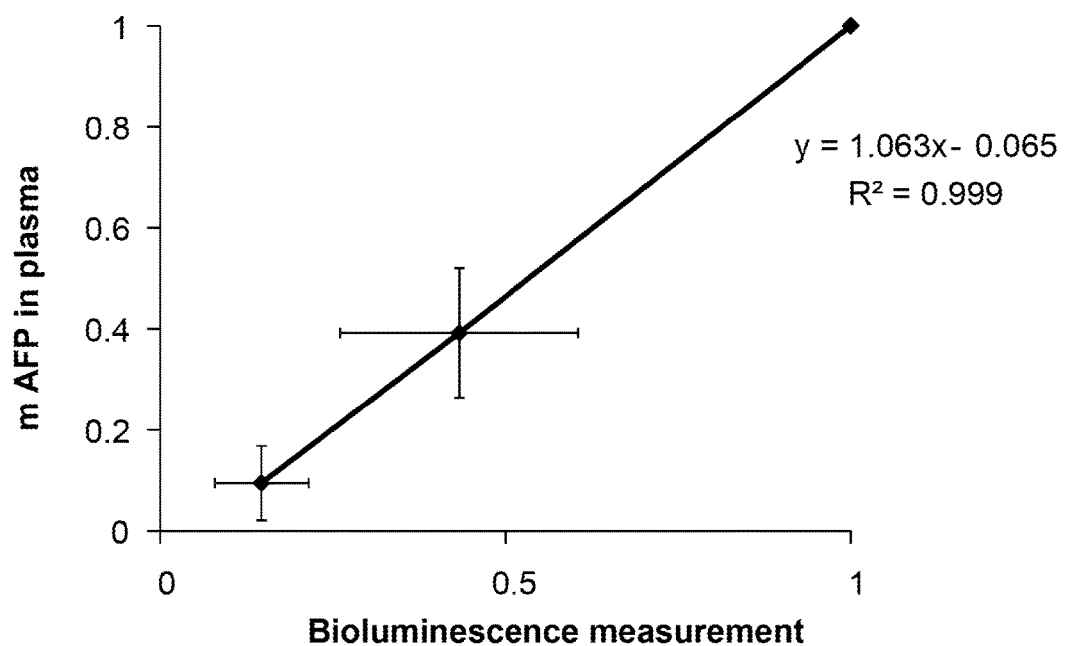
FIG. 5 is a line graph plotting mAFP plasma levels on the Y-axis versus bioluminescence measurement on the X-axis in Hepa 1-6 Luciferase cell-bearing mice. Data were plotted using measurements performed from week 2 to week 4 post tumor implantation.

The Hepa 1-6-Luc mice plasma AFP levels were plotted against the bioluminescence measurements. As shown in FIG. 5, there was a linear relationship between plasma AFP levels and bioluminescence 2-4 weeks post tumor implantation (y=1.063x−0.065; $R^2$=0.999).

Survival studies indicated that all tumor-bearing animals succumbed to progressing liver tumor within 60 days with a median survival of 29 days.

Figure 6:
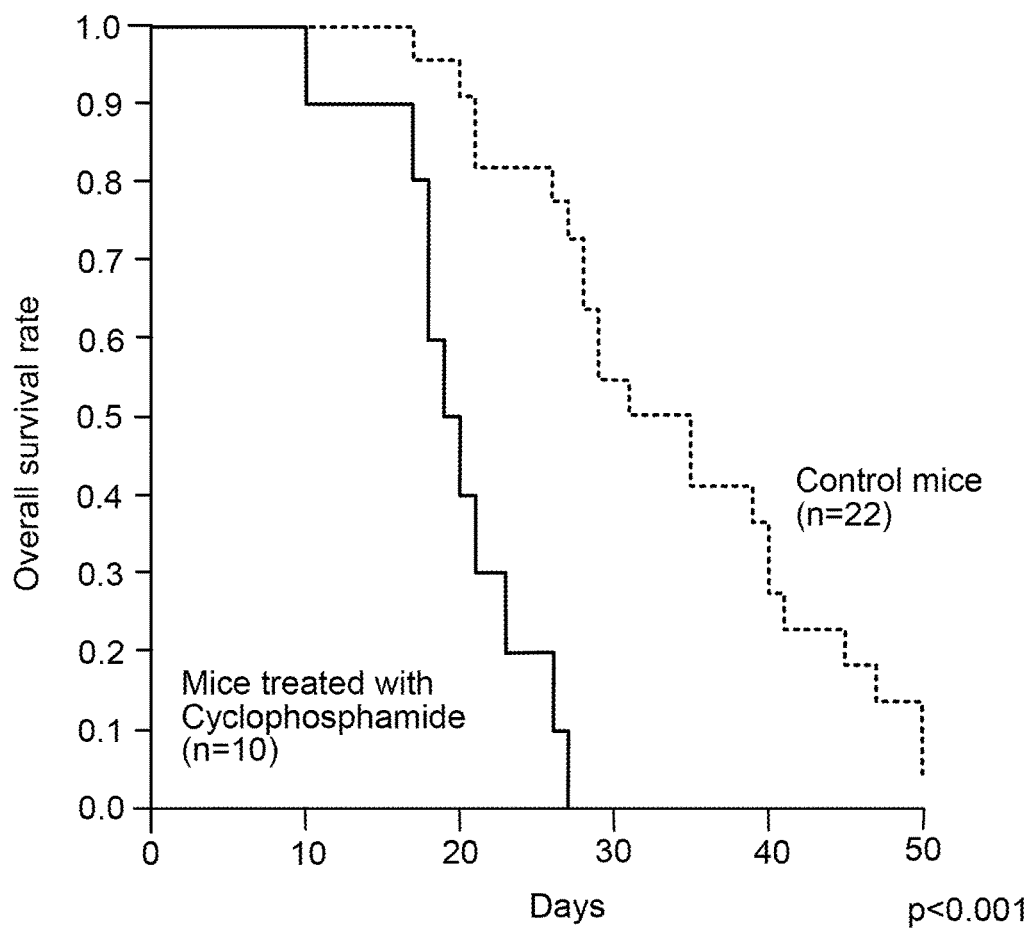
FIG. 6 is a Kaplan-Meier survival curve in Hepa 1-6-tumor bearing mice treated (n=10) or not treated (control, n=22) with cyclophosphamide; p<0.001 when compared using the log rank test.

Treatment with high dose cyclophosphamide to compromise immune responses resulted in a much poorer survival for these animals with a median survival of 19.5 days (FIG. 6, p<0.0001, n=10), compared to control mice (n=22), suggesting that the host immune response was involved in controlling tumor growth.

Example 2: Preparation of Dendritic Cell-Based Vaccine for Hepatocellular Carcinoma This Example describes the preparation of the DC-based vaccine.

Bone marrow-derived DCs were cultured with 20 ng/ml Granulocyte-Macrophage Colony Stimulating Factor (GM-CSF) for one week, pulsed with hepa 1-6 lysates generated from 5 freeze/thaw cycles, and matured with 1 µg/ml LPS (Sigma-Aldrich) overnight.

Figure 7:
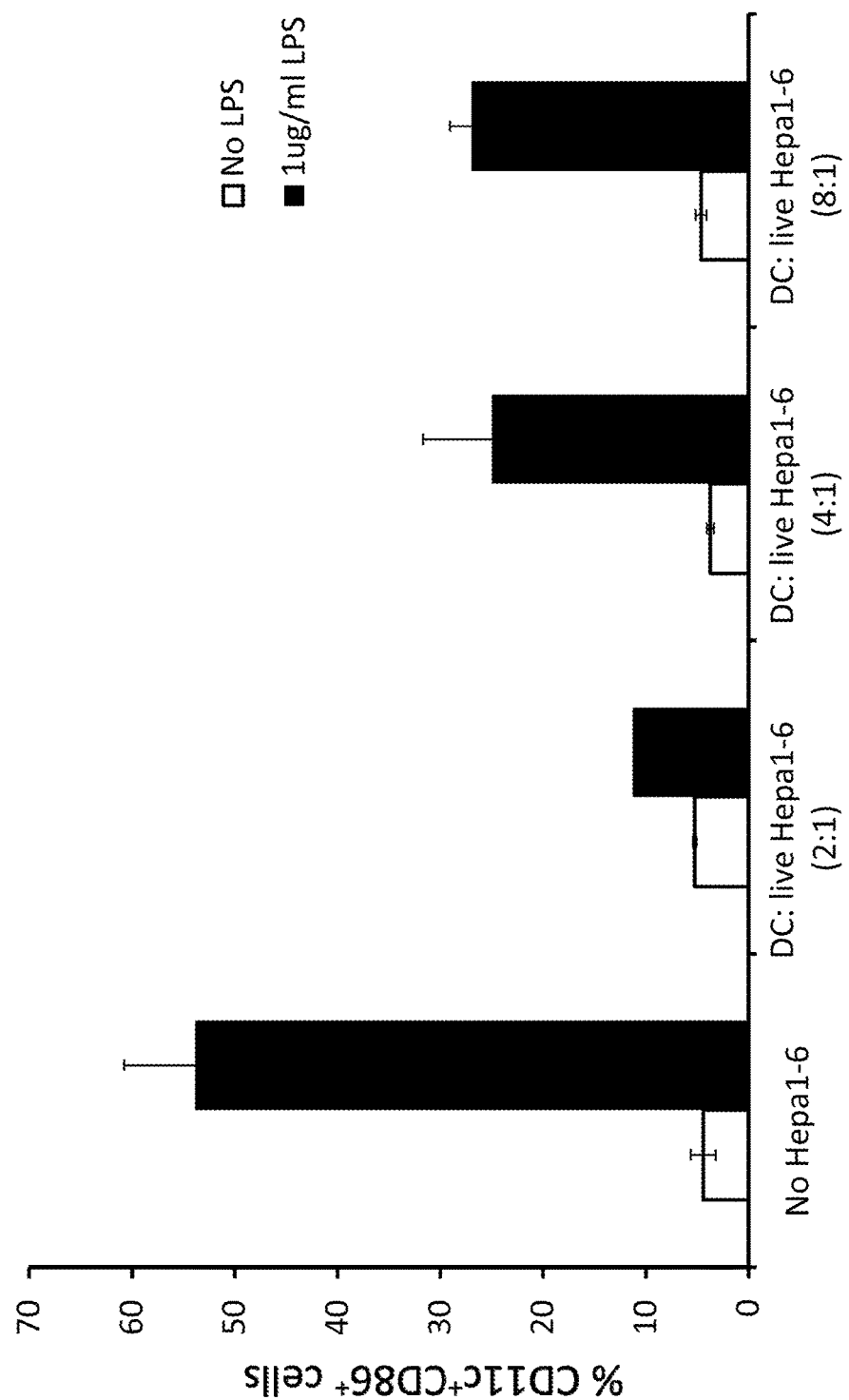
FIG. 7 is a bar graph quantifying the percentages of CD11c+CD86+ cells in DC cultures following incubation: without addition of Hepa 1-6 tumor cells ("No Hepa 1-6"), or with live Hepa 1-6 tumor cells ("DC:live Hepa 1-6") at the indicated ratios of DC:tumor cells. The DCs were cultured in the presence (black bars) or absence (white bars) of 1 µg/ml LPS; n=2-3 in each group.
Figure 8:
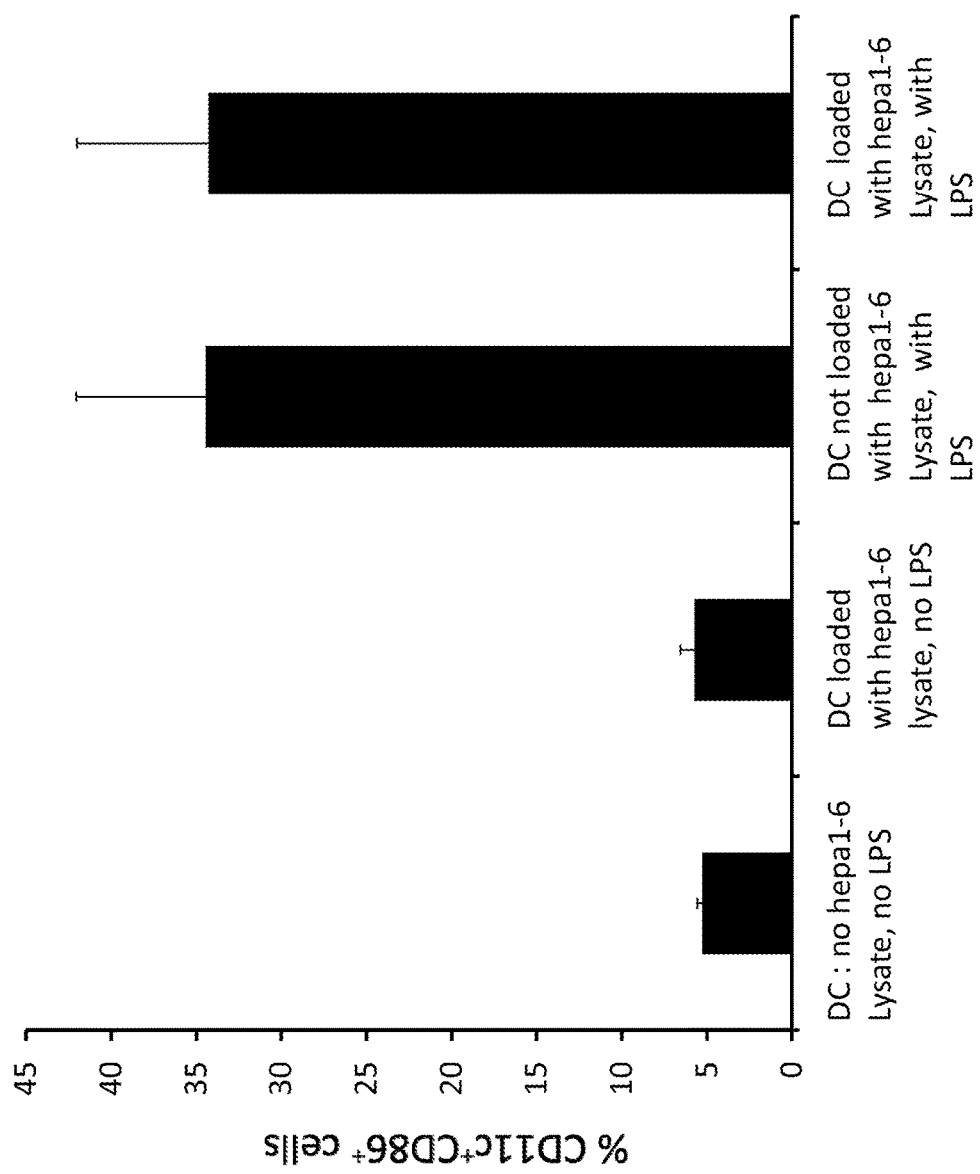
FIG. 8 is a bar graph quantifying the percentages of CD11c+CD86+ cells in DC cultures following incubation in the presence or absence of hepa 1-6 lysate and LPS, as indicated; n=3 in each group.
Figure 9:
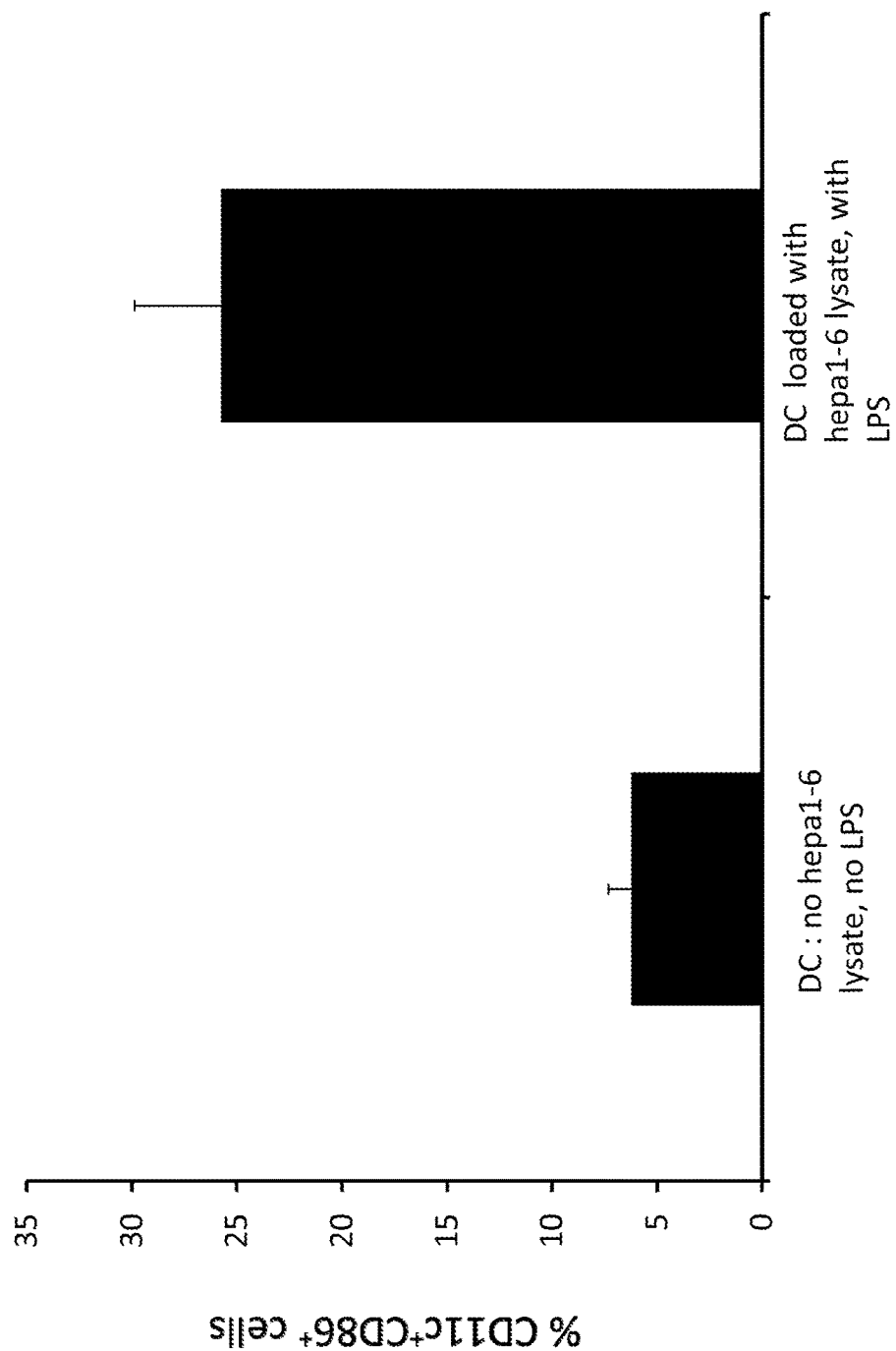
FIG. 9 is a bar graph quantifying the percentages of CD11c+CD86+ cells in DC cultures cultured in the indicated conditions.

Hepa 1-6 lysates prepared by freeze/thaw cycles were used, since, whereas it was determined that live Hepa 1-6 cells inhibited LPS-induced maturation as measured by the expression of the maturation marker CD86 on the CD11c+ DCs (FIG. 7), lysed Hepa 1-6 cells prepared by freeze/thaw cycles did not inhibit the LPS-induced maturation (as measured by CD86 expression) (FIG. 8). Further, whereas only about 7% of the CD11c+ bone marrow DCs expressed CD86 in the absence of LPS and Hepa 1-6 lysate, about 27% of the CD11c+ bone marrow DCs expressed CD86 following maturation with LPS and loading with the Hepa 1-6 lysate (FIG. 9, n=11 in each group).

Example 3: Dendritic Cell-Based Vaccine Treats and Prevents Treats HCC Tumor Growth This example demonstrates that the DC-based HCC vaccine described in Example 2 can treat or prevent HCC.

Hepa 1-6 cells were implanted in the liver, according to the method described in Example 1, and a week later, tumor bearing mice were randomly assigned to receive the DC vaccine described in Example 2 ($2 \times 10^6$ cells, injected intravenously) ("DC vaccine (therapy)," n=40) or vehicle ("no DC vaccine," n=44) or mice were first administered the DC vaccine ($2 \times 10^6$ cells injected intravenously) before implanting the Hepa 1-6 cells ("DC vaccine (prevention)," n=16).

Figure 10:
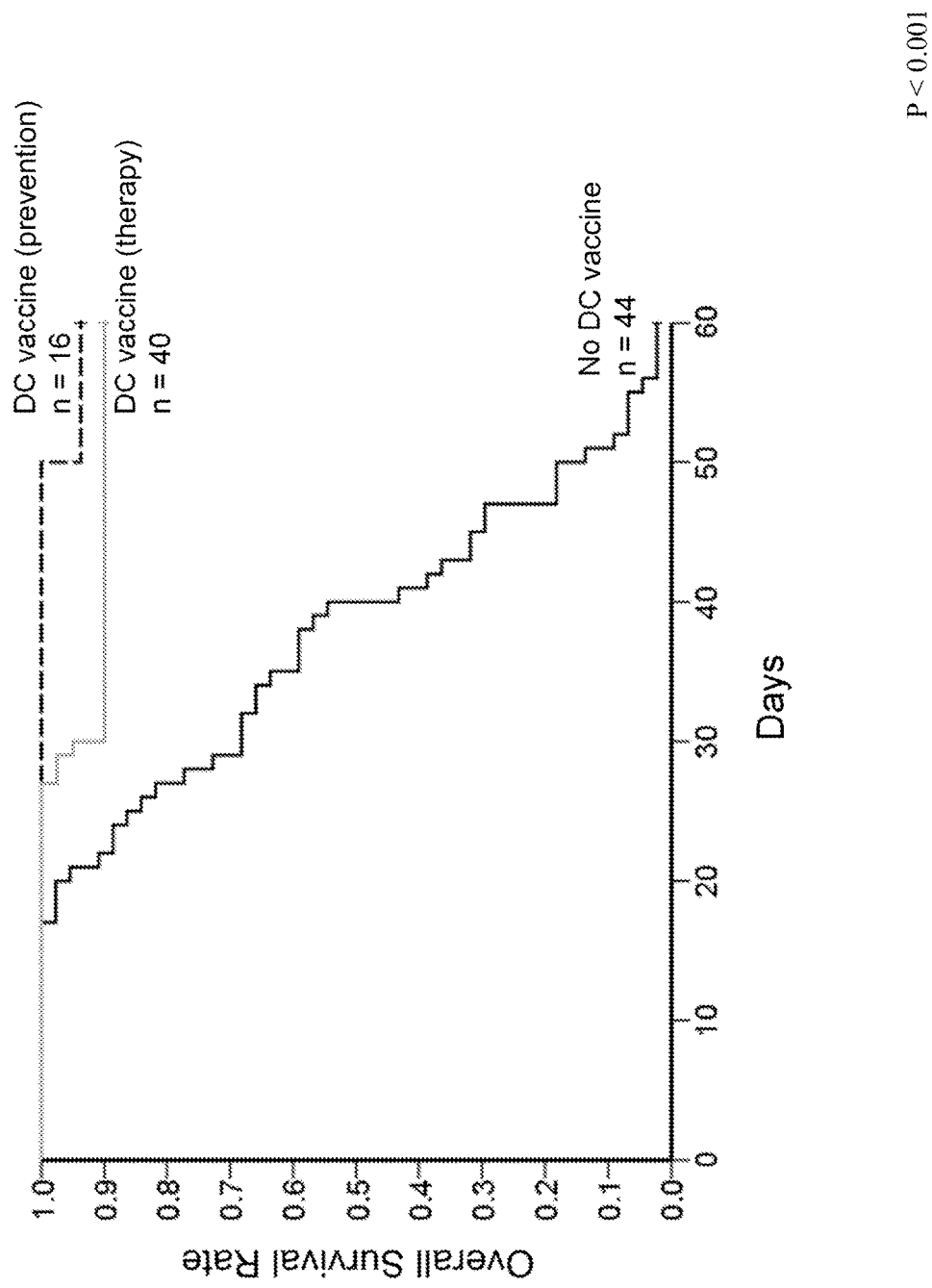
FIG. 10 is a Kaplan-Meier survival curve in Hepa 1-6-tumor bearing mice administered the DC vaccine either before ("DC vaccine (prevention)," n=16) or after ("DC vaccine (therapy)," n=40) implantation of Hepa 1-6 cells or in mice that were not administered the DC vaccine ("No DC vaccine," n=44); p<0.001 when comparing "DC vaccine (prevention)" group or "DC vaccine (therapy)" group to "No DC vaccine group" (log rank test).

Mice treated with the DC vaccine after Hepa 1-6 tumors were established (therapy) all survived for up to 60 days (FIG. 10). Further, mice that were vaccinated with the DC vaccine before implanting the Hepa 1-6 cells (prevention), had 100% survival, suggesting that the vaccine could prevent development of HCC (FIG. 10).

Figure 11:
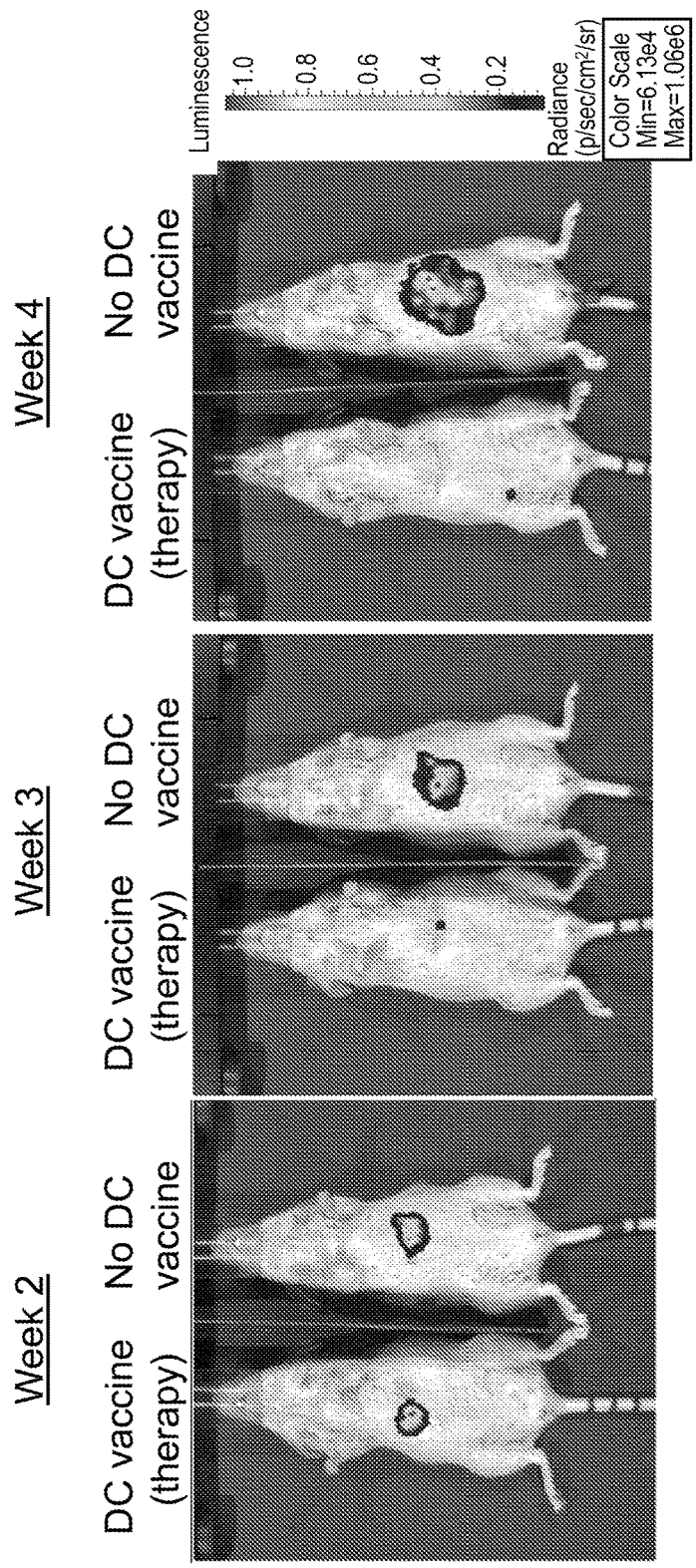
FIG. 11 contains bioluminescence images at weeks 2, 3 and 4 post-implantation of Hepa 1-6-luciferase cells in mice treated or not treated with the DC vaccine described in Example 2 following implantation of the Hepa 1-6-luc cells.
Figure 12:
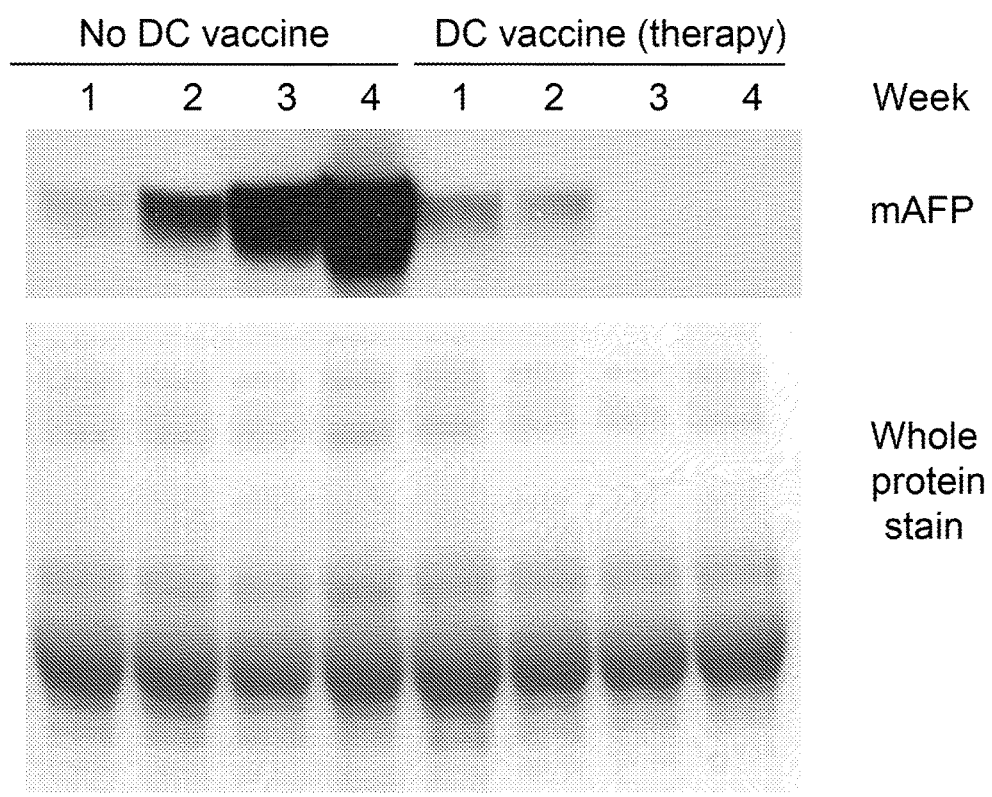
FIG. 12 is a photograph of a Western blot result for murine AFP (mAFP) protein expression in liver cells from Hepa 1-6 bearing mice not treated (leftmost lanes 1 to 4, showing result for individual mice in each lane) or treated (rightmost lanes 1 to 4, showing result for individual mice in each lane) with the DC vaccine described in Example 2 following implantation of Hepa 1-6 cells. The photograph is overlaid on a photograph of the Western blot result of a whole protein stain for the same samples.

The DC vaccine also inhibited tumor progression in mice bearing Hepa 1-6 tumors, as determined by bioluminescence imaging (described in Example 1, above) (FIG. 11). The improved survival and inhibition of tumor progression correlated with a decrease in circulating murine AFP levels in these mice, while in untreated mice, mAFP in plasma increased as tumor progressed and test animals succumbed to disease (FIG. 12).

Example 4: Role for T Regulatory Cells in HCC

This Example demonstrates that FoxP3, a marker expressed in T regulatory cells, is upregulated within the liver tumors of HCC patients, and that the DC vaccine prevents the accumulation of Foxp3$^+$ Treg within Hepa 1-6 tumors in the HCC model described in Example 1.

Materials and Methods:

Human FoxP3: Human tumor samples and paired non-neoplastic liver were collected post-operatively. Surgical resection tissue specimens were used for RNA extraction using the RNeasy Mini Kit (Qiagen) according to manufacturers' protocols. cDNA was generated through reverse transcription, and Foxp3 mRNA level was quantify by real-time PCR using the following primer sequence: forward: 5'-AGAAGCAGCGTCAGTACCCCT-3' (SEQ ID NO: 3), reverse: 5'-CTGCACGGGACTCAAGAGAC-3' (SEQ ID NO: 4).

FoxP3 Tregs in mouse model: Single cell suspension from tumor was prepared by digesting tumor tissue specimens with a mixture of enzymes containing collagenase type I (0.05 mg/ml), collagenase type IV (0.05 mg/ml), hyaluronidase (0.025 mg/ml) (all from Sigma), DNase I (0.01 mg/ml), and soybean trypsin inhibitor (0.2 trypsin soybean inhibitor units/ml) (Boehringer Mannheim) for 15 min at 37° C. Lymphocytes were enriched by layering the single cell suspension on the LSM lymphocyte separation medium (MP), followed by centrifugation at 400×g at room temperature for 20 minutes. The lymphocyte layer was collected, washed and stained for cell surface CD4 and CD8 (eBioscience). Intracellular Foxp3 staining was performed according to manufacturers' instructions (eBioscience). Flow cytometry was performed using a FACScan caliber (Becton Dickenson).

Figure 13:
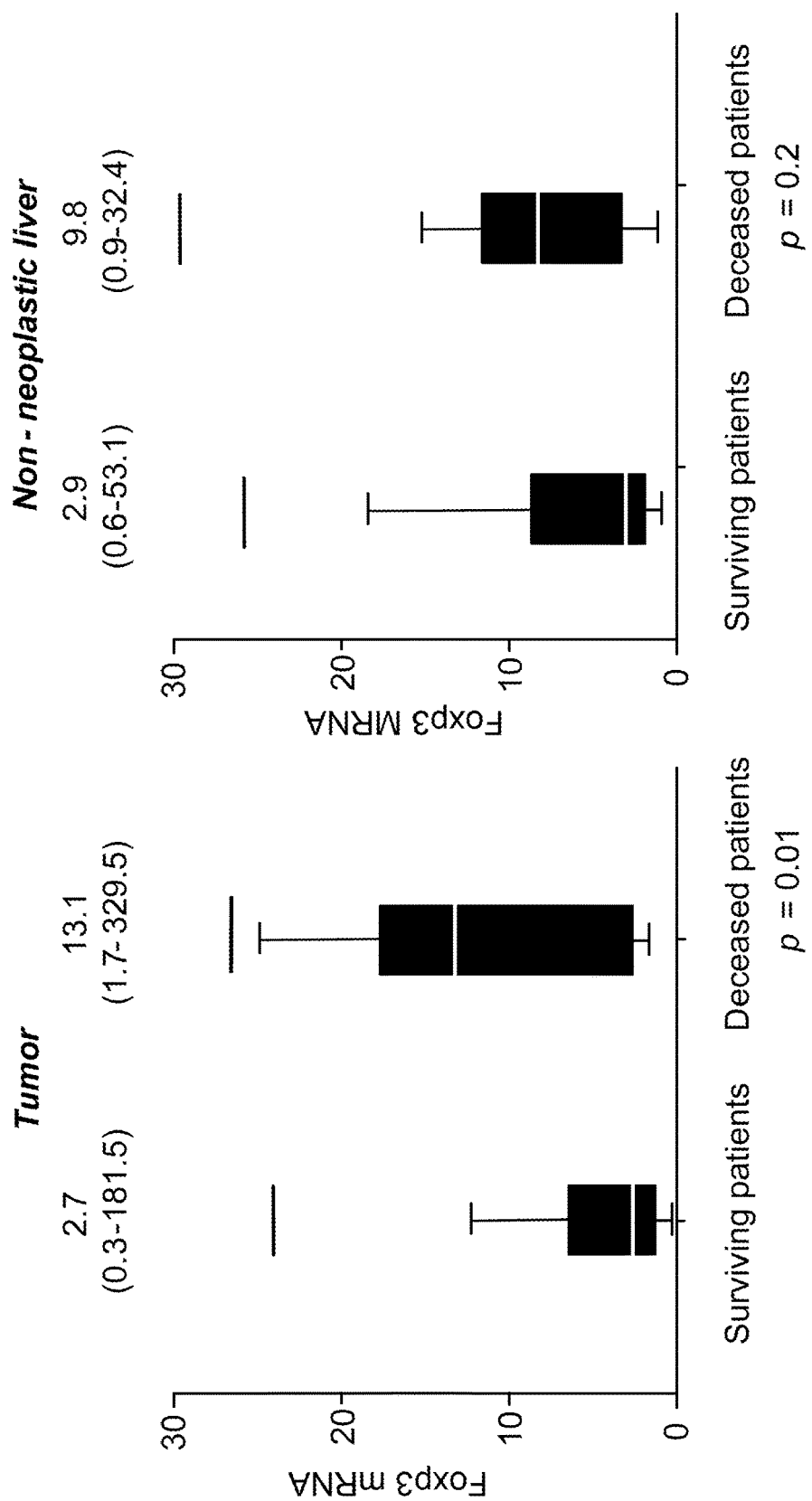
FIG. 13 shows the level of Foxp3 mRNA expression in liver tumor tissue or non-neoplastic liver tissue obtained following surgical resection. Higher Foxp3 mRNA was observed in patients who were deceased at the time of analysis. Box-plot graphs are shown indicating quartile distribution of Foxp3 mRNA for each group included. Lower limits box plots $25^{th}$ percentile, line within box plot indicates median, and higher limit of box plot indicates $75^{th}$ percentile of Foxp3 mRNA. Median values are indicated above each group. P values are indicated on the graph (Mann-Whitney U test).
Figure 14:
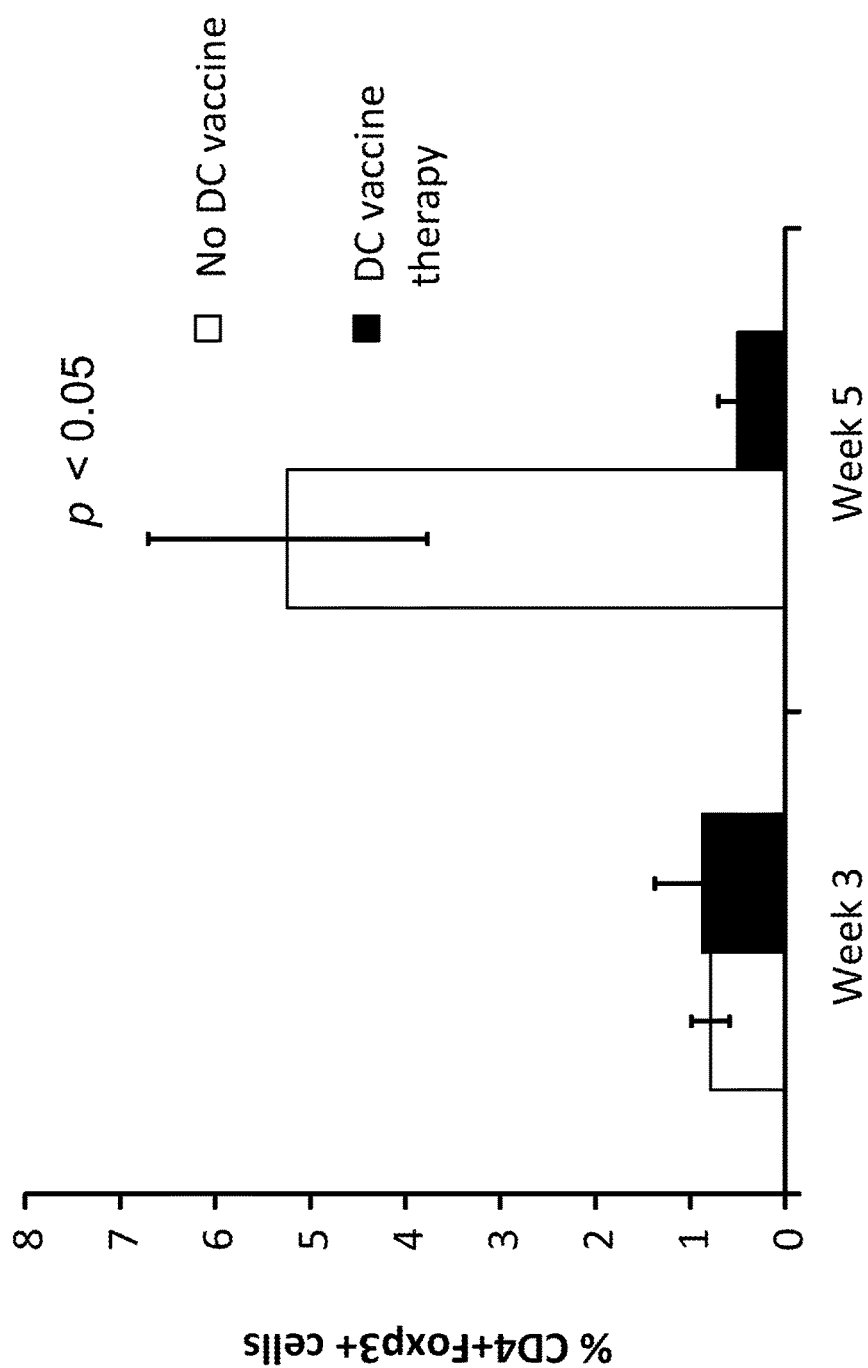
FIG. 14 is a bar graph quantifying the percentage of CD4+Foxp3+ cells relative to the total enriched population of tumor infiltrating lymphocytes in the tumor at the indicated time points in the liver tumors of Hepa 1-6 cell-bearing mice that were treated one week after tumor implantation ("DC vaccine therapy") or not treated ("No DC vaccine") with the DC vaccine following implantation of the Hepa 1-6 cells.

Results:

The expression of FoxP3 in tumors of human hepatitis B (HBV)-associated HCC patients was determined and correlated with survival and compared with liver samples of non-neoplastic livers. As shown in FIG. 13, Foxp3 mRNA (shown as relative expression) within the tumors of HCC patients was associated with mortality (2.7 versus 13.1 in tumors of surviving patients compared to deceased patients, FIG. 13). It was also determined that the DC vaccine (prepared as described in Example 2) affected the frequency of Foxp3+Tregs in the Hepa 1-6 tumors in the HCC model. As shown in FIG. 14, the DC vaccine reduced the accumulation of Foxp3$^+$ Tregs within Hepa 1-6 tumors.

Figure 15:
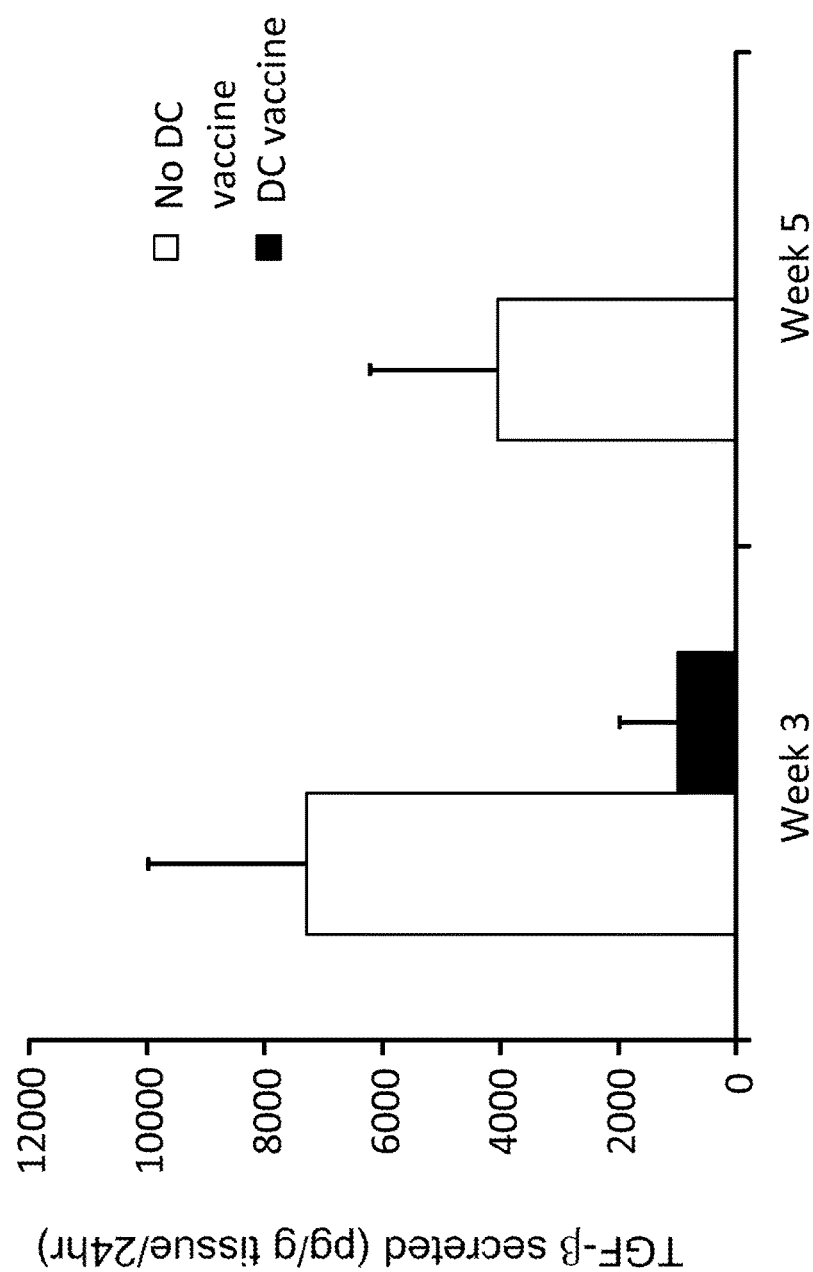
FIG. 15 is a bar graph quantifying the levels of TFGβ secreted from the tumor tissue (pg/g tissue/24 hours) at the indicated time points of Hepa 1-6 cell-bearing mice that were treated ("DC vaccine therapy") or not treated ("No DC vaccine") with the DC vaccine following implantation of the Hepa 1-6 cells.

Consistent with the observed decrease in Treg in the tumor, the secretion of TGF-β, which is secreted by Tregs and other cell types within the tumor, was inhibited in tumors of mice that had been administered the DC vaccine (FIG. 15). Orthotopic Hepa 1-6 tumors secrete large amount of TGF-β. TGF-β is a multifunctional cytokine that influences many biological processes during HCC initiation, progression and metastasis, and persistently high levels of TGF-β promote malignancy and metastasis. TGF-β expression is often elevated in patients with HCC, and high levels of circulating TGF-β is associated with invasive types of HCC and poor survival. TGF-β within the tumor microenvironment also promotes Treg accumulation. TGF-β regulates the development of natural Tregs in the thymus during negative selection, and is required for the conversion of conventional T cells into inducible Tregs at extrathymical site including tumor. In addition, TGF-β leads to Treg recruitment into HCC through enhanced production of CCL22, a chemokine for Tregs, and this pathway is associated with venous metastasis of HBV-HCC. Therefore, inhibition of TGF-β production and Treg accumulation may underlie the anti-tumor effect of the DC vaccine.

Figure 16:
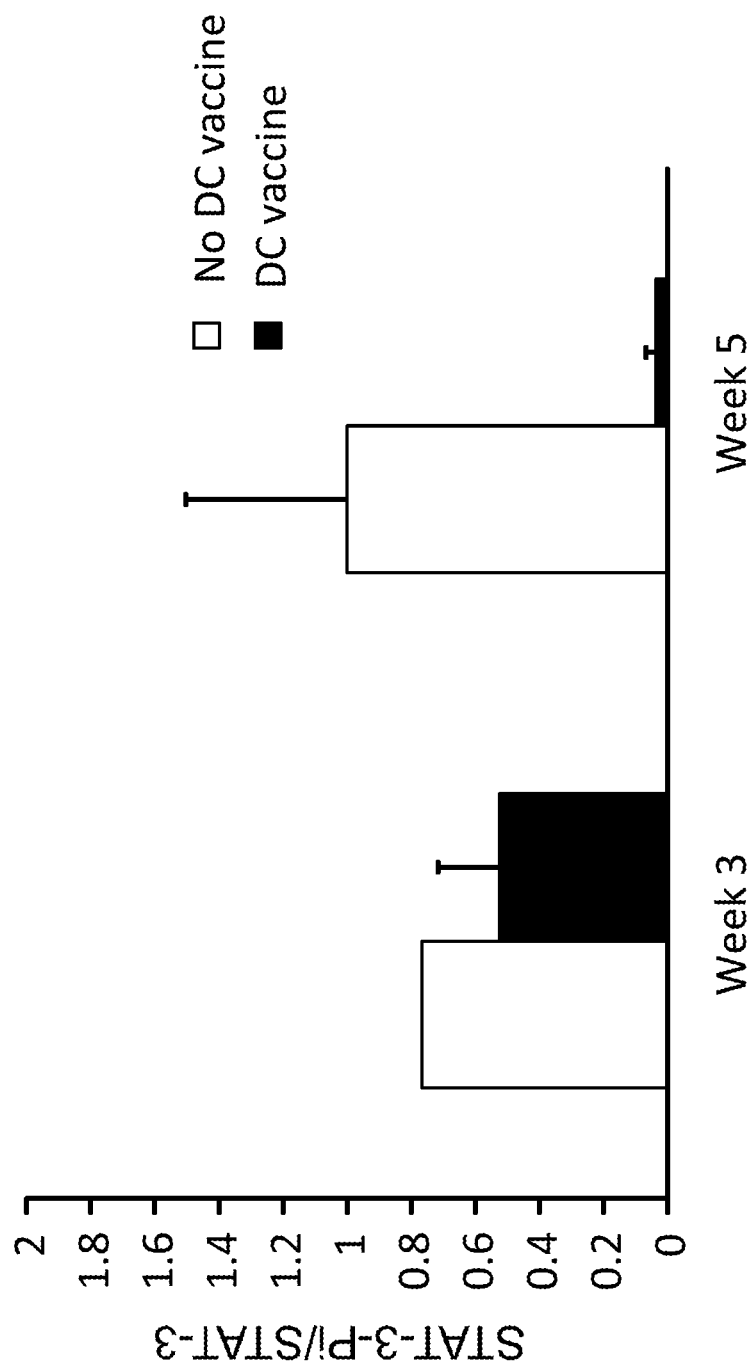
FIG. 16 is a bar graph quantifying the ratio of phospho-STAT-3 to STAT-3 at the indicated time points in the tumors of Hepa 1-6 cell-bearing mice that were treated ("DC vaccine therapy") or not treated ("No DC vaccine") with the DC vaccine following implantation of the Hepa 1-6 cells.

Furthermore, signal transducer and activator of transcription 3 (STAT3), is a transcription factor which is associated with cancer. Interestingly, STAT-3 activation was inhibited in the tumor following administration of the DC vaccine (FIG. 16). STAT3 is a transcription factor, and activation occurs via phosphorylation and dimerization of tyrosine residue (Tyr705), leading to nuclear entry and binding to the promoter regions of its target genes including Bcl-XL. By regulating its downstream gene transcription, STAT3 is critical for promoting cell cycle progression and/or cell survival. STAT3 activation occurs following cytokine stimulation, and constitutive activation of STAT3 has been demonstrated to contribute to tumorigenesis, angiogenesis, tumor progression in hepatocellular carcinoma. Therefore, inhibition of STAT3 phosphorylation and activation within the tumor indicated dampened responses downstream of STAT3 activation such as tumor cell survival, proliferation and angiogenesis.

Prophetic Example 1: Clinical Trial

This Examples describes a clinical trial with a DC-based vaccine in HCC patients.

The targeted enrollment number for this phase I trial is nine HBV-HCC patients with safety being the primary end point, and immunology being the second end point.

Patient tissues are collected following surgical resection and blood is drawn according to the schema below. Blood is processed for plasma, serum, and PBMC isolation. Tissue specimens following liver resection are submitted to the clinical pathology lab for histology, and a small portion of tissues from four different locations (tumor, tumor periphery, non-neoplastic liver adjacent to tumor, and distant non-neoplastic liver) are collected for research purposes. Upon collection, tissues are processed for DNA and RNA isolation. All processed blood and tissue samples as well as un-processed tissue pieces are stored in liquid nitrogen. All sample collection and procession procedures meet the NCI Office of Biorepositories and Biospecimen Research Best Practices. Histologic specimens are assessed for the degree of fibrosis using the Ishak method (0-6) (see, Goodman Z D. Grading and staging systems for inflammation and fibrosis in chronic liver diseases. Journal of Hepatology 2007; 47(4):598-607). Tumor tissues are processed to obtain autologous tumor cell lysates.

For the preparation of autologous tumor cell lysates, fresh resected tumor tissues are dissociated into 5-mm$^3$ pieces under sterile conditions. 1 gram of tumor tissues is digested in a minimum volume of 40 ml of a protease mixture that consists of HBSS, 2.5 U/ml hyaluronidase type V, 0.5 mg/ml collagenase type IV, and 0.05 mg/ml deoxyribonuclease type I. The digestion is performed at room temperature with constant stirring in a trypsinizing flask for 2 to 6 hours. The resulting cell suspension is filtered through a layer of number 70 nylon mesh. Cells are washed two times in HBSS and resuspended in 0.5 ml HBSS and counted. Cells are resuspended in 90% human AB serum plus 10% DMSO to reach a final concentration of $10^6$ cells/ml. 1 ml cell suspension is aliquotted into cryo vials, and the cells are frozen in liquid nitrogen. The frozen autologous tumors are thawed by immersing in a 37° C. water bath for 2 minutes. The thawed cells are then placed in liquid nitrogen to quickly freeze the cells again. This freeze/thaw cycle is carried out a total of 5 times to obtain the tumor cell lysate.

After surgical resection, the patients are scheduled for unmobilized leukapheresis procedure to collect peripheral blood mononuclear cells (MNC). The goal of the MNC collection is to collect a product that meets the following specifications:

White Blood Cell (WBC) content: $\geq 5 \times 10^9$ to $30 \times 10^9$;
Monocyte content: $\geq 1 \times 10^9$;
Granulocyte content: <3%;
Red Blood Cell (RBC) content: <7.5 mL (otherwise RBC debulking is recommended).

Standard operating procedures for the collection of human PBMC are known in the art and described, e.g., in Phuphanich S, et al. Cancer Immunol Immunother. 2013 January; 62(1):125-35. Next, the PBMCs are cultured according to the following protocol to generate DCs.

The DCs are differentiated from PBMCs in an 8-day procedure. On Day 0, the PBMCs are thawed and plated in RPMI-1640 medium containing 1% autologous plasma onto tissue culture flasks to select for monocytes, which adhere to the plastic surface after a one hour incubation step at 37° C. Lymphocytes are washed off the flasks, and the monocytes (adherent CD14+ cells) are then cultured for 5 days in the presence of 20 ng/ml GM-CSF (Bayer Healthcare Pharmaceuticals), with or without 400 IU/ul [60 ng/ul] IL-4). During this period, the monocytes differentiate into immature DCs (non-adherent, CD14− CD83− cells).

On Day 5, the immature DCs are harvested by vigorously swirling the flasks, and by pipetting up and down to resuspend non-adherent and loosely adherent cells. The DCs are washed, and transferred to 6-well plates. On Day 6, tumor cell lysates are added to the tissue culture wells in a ratio of lysate of 1 tumor cell to 5 DCs. One hour later, 1 µg/ml LPS (Sigma-Aldrich) was added to the cells and incubated for 18-24 hours.

Next, the DCs are washed and resuspended in 5 ml sterile 0.9% NaCl, USP and then each tube is brought to 14 ml with more PBS. One batch of the cell is resuspended in the DC freezing media and another batch is resuspended in injection solution (sterile saline). In most cases, the volumes are 2 ml for freezing and 4 ml for injection (sterile saline). The cells can then be cryofrozen for future use or used immediately. Quality control testing is performed afterwards, usually the following day, on frozen control aliquots. If release criteria are met, frozen aliquots designated for injection can be thawed as needed and administered to the patient. This method has been validated to ensure potency and stability of the cells by testing batches of frozen/thawed DCs for immunostimulatory capacity and for viability under transport conditions. Frozen/thawed DCs routinely stimulated antigen-specific T cell clones just as well as freshly prepared DCs using a controlled-rate freezer. Thawed DCs are stable for at least two hours in injection solution when kept on ice.

QC ("release") criteria include >70% viable cells, negative results for all sterility and endotoxin tests, and >50% of the cells having the characteristics of mature DCs by flow cytometry (large, CD14− CD83+ cells). Close to 80% mature DCs, are routinely obtained with this method, with most of the remaining cells being lymphocytes. Cell viability is typically >90%.

For immune monitoring purposes, an aliquot of DCs without antigen loading and DCs loaded with autologous tumor lysates are stored. Quality control testing is performed the following day.

The patients are then scheduled for up to six DC vaccine injections. The DC vaccine is administered to the patients intravenously through a transfusion set in five to ten minutes. The patients are observed for 2 hours after vaccination to assess immediate complications. Toxicity is graded according to World Health Organization common toxicity criteria. Safety is monitored via clinical assessment, serial full blood count and biochemistry. Patients are followed after vaccine treatment through imaging and immune monitoring. A schema showing the vaccination protocol is illustrated in FIG. 17.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all values are approximate, and are provided for description.

Patents, patent applications, publications, product descriptions, and protocols are cited throughout this application, the disclosures of which are incorporated herein by reference in their entireties for all purposes.

What is claimed is:

1. An immunogenic composition consisting of dendritic cells (DCs) (i) autologous to a subject with a liver tumor, (ii) matured in the presence of lipopolysaccharide as the only maturation agent, (iii) loaded with hepatocellular (HCC) tumor cell lysate prepared by performing repeated freeze-thaw cycles of liver tumor cells obtained from the subject, and (iv) a pharmaceutically acceptable carrier or excipient; and
wherein the DCs selectively reduce T regulatory cells (Tregs) in the liver tumor when administered to the subject.

2. The composition of claim 1, wherein the immunogenic composition is a vaccine.

3. The composition of claim 1, wherein the Tregs are FoxP3+.

4. The composition of claim 1, wherein the DCs are prepared from peripheral blood mononuclear cells (PBMCs).

5. The composition of claim 1, wherein the lipopolysaccharide is present at a concentration of 1 µg/ml.

6. The composition of claim 1, wherein the composition consists of 1×10$^7$ DCs.

7. The composition of claim 1, wherein the subject is human.

8. The composition of claim 1, wherein the HCC tumor cells are obtained from the subject by surgical resection, percutaneous needle biopsy, or laparoscopic tumor biopsy/excision.

9. The composition of claim 4, wherein the PBMCs are cultured in the presence of granulocyte-macrophage colony-stimulating factor.

10. The composition of claim 4, wherein the PBMCs are cultured in the presence of IL-4.

* * * * *

SEQUENCE LISTING

<160> NUMBER OF SEQ ID NOS: 4

<210> SEQ ID NO 1
<211> LENGTH: 2397

```
<212> TYPE: DNA
<213> ORGANISM: Homo Sapien

<400> SEQUENCE: 1
gcacacactc atcgaaaaaa atttggatta ttagaagaga gaggtctgcg gcttccacac      60
cgtacagcgt ggttttttctt ctcggtataa aagcaaagtt gttttttgata cgtgacagtt     120 tcccacaagc caggctgatc cttttctgtc agtccacttc accaagcctg cccttggaca     180
aggacccgat gcccaacccc aggcctggca agccctcggc cccttccttg gcccttggcc     240
catccccagg agcctcgccc agctggaggg ctgcacccaa agcctcagac ctgctggggg     300 cccgggggccc aggggggaacc ttccagggcc gagatcttcg aggcggggcc catgcctcct     360
cttcttcctt gaaccccatg ccaccatcgc agctgcagct gcccacactg cccctagtca     420
tggtggcacc ctccggggca cggctgggcc ccttgcccca cttacaggca ctcctccagg     480
acaggccaca tttcatgcac cagctctcaa cggtggatgc ccacgcccgg accctgtgc     540 tgcaggtgca cccctggag agcccagcca tgatcagcct cacaccaccc accaccgcca     600
ctggggtctt ctccctcaag gcccggcctg gcctcccacc tgggatcaac gtggccagcc     660
tggaatgggt gtccagggag ccggcactgc tctgcacctt cccaaatccc agtgcaccca     720
ggaaggacag cacccttcg gctgtgcccc agagctccta cccactgctg gcaaatggtg     780
tctgcaagtg gcccggatgt gagaaggtct tcgaagagcc agaggacttc ctcaagcact     840
gccaggcgga ccatcttctg gatgagaagg gcagggcaca atgtctcctc cagagagaga     900
tggtacagtc tctggagcag cagctggtgc tggagaagga gaagctgagt gccatgcagg     960
cccacctggc tgggaaaatg gcactgacca aggcttcatc tgtggcatca tccgacaagg    1020
gctcctgctg catcgtagct gctggcagcc aaggccctgt cgtcccagcc tggtctggcc    1080
cccgggaggc ccctgacagc ctgtttgctg tccggaggca cctgtggggt agccatggaa    1140
acagcacatt cccagagttc ctccacaaca tggactactt caagttccac aacatgcgac    1200 ccccttttcac ctacgccacg ctcatccgct gggccatcct ggaggctcca gagaagcagc    1260
ggacactcaa tgagatctac cactggttca cacgcatgtt tgccttcttc agaaaccatc    1320
ctgccacctg gaagaacgcc atccgccaca acctgagtct gcacaagtgc tttgtgcggg    1380
tggagagcga gaaggggggct gtgtggaccg tggatgagct ggagttccgc aagaaacgga    1440
gccagaggcc cagcaggtgt tccaacccta cacctggccc ctgacctcaa gatcaaggaa    1500
aggaggatgg acgaacaggg gccaaactgg tgggaggcag aggtggtggg ggcagggatg    1560
ataggccctg gatgtgccca cagggaccaa gaagtgaggt ttccactgtc ttgcctgcca    1620
gggcccctgt tccccgctg gcagccaccc cctccccat catatccttt gccccaaggc    1680
tgctcagagg ggccccggtc ctggccccag ccccccacctc cgcccagac accccccca    1740 gtcgagccct gcagccaaac agagccttca caaccagcca cacagagcct gcctcagctg    1800
ctcgcacaga ttacttcagg gctggaaaag tcacacagac acacaaaatg tcacaatcct    1860
gtccctcact caacacaaac cccaaaacac agagagcctg cctcagtaca ctcaaacaac    1920
ctcaaagctg catcatcaca caatcacaca caagcacagc cctgacaacc cacacacccc    1980
aaggcacgca cccacagcca gcctcagggc ccacaggggg actgtcaaca cagggggtgtg    2040 cccagaggcc tacacagaag cagcgtcagt accctcagga tctgaggtcc caacacgtgc    2100
tcgctcacac acacggcctg ttagaattca cctgtgtatc tcacgcatat gcacacgcac    2160
agccccccag tgggtctctt gagtcccgtg cagacacaca cagccacaca cactgccttg    2220
```

-continued

```
ccaaaaatac  cccgtgtctc  ccctgccact  cacctcactc  ccattccctg  agccctgatc    2280
catgcctcag  cttagactgc  agaggaacta  ctcatttatt  tgggatccaa  ggccccaac    2340 ccacagtacc  gtccccaata  aactgcagcc  gagctcccca  caaaaaaaaa  aaaaaaa      2397
```

<210> SEQ ID NO 2
<211> LENGTH: 431
<212> TYPE: PRT
<213> ORGANISM: Homo sapien

<400> SEQUENCE: 2

| | | | | | | | | | | | | | | |
|---|---|---|---|---|---|---|---|---|---|---|---|---|---|---|
| Met | Pro | Asn | Pro | Arg | Pro | Gly | Lys | Pro | Ser | Ala | Pro | Ser | Leu | Ala | Leu |
| 1 | | | | 5 | | | | | 10 | | | | | 15 | |
| Gly | Pro | Ser | Pro | Gly | Ala | Ser | Pro | Ser | Trp | Arg | Ala | Ala | Pro | Lys | Ala |
| | | | 20 | | | | | 25 | | | | | 30 | | |
| Ser | Asp | Leu | Leu | Gly | Ala | Arg | Gly | Pro | Gly | Gly | Thr | Phe | Gln | Gly | Arg |
| | | | | 35 | | | | | 40 | | | | | 45 | |
| Asp | Leu | Arg | Gly | Gly | Ala | His | Ala | Ser | Ser | Ser | Leu | Asn | Pro | Met | |
| | 50 | | | | | 55 | | | | | 60 | | | | |
| Pro | Pro | Ser | Gln | Leu | Gln | Leu | Pro | Thr | Leu | Pro | Leu | Val | Met | Val | Ala |
| 65 | | | | | 70 | | | | | 75 | | | | | 80 |
| Pro | Ser | Gly | Ala | Arg | Leu | Gly | Pro | Leu | Pro | His | Leu | Gln | Ala | Leu | Leu |
| | | | | 85 | | | | | 90 | | | | | 95 | |
| Gln | Asp | Arg | Pro | His | Phe | Met | His | Gln | Leu | Ser | Thr | Val | Asp | Ala | His |
| | | | 100 | | | | | 105 | | | | | 110 | | |
| Ala | Arg | Thr | Pro | Val | Leu | Gln | Val | His | Pro | Leu | Glu | Ser | Pro | Ala | Met |
| | | | 115 | | | | | 120 | | | | | 125 | | |
| Ile | Ser | Leu | Thr | Pro | Pro | Thr | Thr | Ala | Thr | Gly | Val | Phe | Ser | Leu | Lys |
| | | 130 | | | | | 135 | | | | | 140 | | | |
| Ala | Arg | Pro | Gly | Leu | Pro | Pro | Gly | Ile | Asn | Val | Ala | Ser | Leu | Glu | Trp |
| 145 | | | | | 150 | | | | | 155 | | | | | 160 |
| Val | Ser | Arg | Glu | Pro | Ala | Leu | Leu | Cys | Thr | Phe | Pro | Asn | Pro | Ser | Ala |
| | | | | 165 | | | | | 170 | | | | | 175 | |
| Pro | Arg | Lys | Asp | Ser | Thr | Leu | Ser | Ala | Val | Pro | Gln | Ser | Ser | Tyr | Pro |
| | | | 180 | | | | | 185 | | | | | 190 | | |
| Leu | Leu | Ala | Asn | Gly | Val | Cys | Lys | Trp | Pro | Gly | Cys | Glu | Lys | Val | Phe |
| | | | 195 | | | | | 200 | | | | | 205 | | |
| Glu | Glu | Pro | Glu | Asp | Phe | Leu | Lys | His | Cys | Gln | Ala | Asp | His | Leu | Leu |
| | | 210 | | | | | 215 | | | | | 220 | | | |
| Asp | Glu | Lys | Gly | Arg | Ala | Gln | Cys | Leu | Leu | Gln | Arg | Glu | Met | Val | Gln |
| 225 | | | | | 230 | | | | | 235 | | | | | 240 |
| Ser | Leu | Glu | Gln | Gln | Leu | Val | Leu | Glu | Lys | Glu | Lys | Leu | Ser | Ala | Met |
| | | | | 245 | | | | | 250 | | | | | 255 | |
| Gln | Ala | His | Leu | Ala | Gly | Lys | Met | Ala | Leu | Thr | Lys | Ala | Ser | Ser | Val |
| | | | 260 | | | | | 265 | | | | | 270 | | |
| Ala | Ser | Ser | Asp | Lys | Gly | Ser | Cys | Cys | Ile | Val | Ala | Ala | Gly | Ser | Gln |
| | | | 275 | | | | | 280 | | | | | 285 | | |
| Gly | Pro | Val | Val | Pro | Ala | Trp | Ser | Gly | Pro | Arg | Glu | Ala | Pro | Asp | Ser |
| | | 290 | | | | | 295 | | | | | 300 | | | |
| Leu | Phe | Ala | Val | Arg | Arg | His | Leu | Trp | Gly | Ser | His | Gly | Asn | Ser | Thr |
| 305 | | | | | 310 | | | | | 315 | | | | | 320 |
| Phe | Pro | Glu | Phe | Leu | His | Asn | Met | Asp | Tyr | Phe | Lys | Phe | His | Asn | Met |
| | | | | 325 | | | | | 330 | | | | | 335 | |
| Arg | Pro | Pro | Phe | Thr | Tyr | Ala | Thr | Leu | Ile | Arg | Trp | Ala | Ile | Leu | Glu |
| | | | 340 | | | | | 345 | | | | | 350 | | |

```
Ala Pro Glu Lys Gln Arg Thr Leu Asn Glu Ile Tyr His Trp Phe Thr
        355                 360                 365

Arg Met Phe Ala Phe Arg Asn His Pro Ala Thr Trp Lys Asn Ala
    370             375                 380

Ile Arg His Asn Leu Ser Leu His Lys Cys Phe Val Arg Val Glu Ser
385             390             395                 400

Glu Lys Gly Ala Val Trp Thr Val Asp Glu Leu Glu Phe Arg Lys Lys
                405             410                 415

Arg Ser Gln Arg Pro Ser Arg Cys Ser Asn Pro Thr Pro Gly Pro
                420             425             430

<210> SEQ ID NO 3
<211> LENGTH: 21
<212> TYPE: DNA
<213> ORGANISM: Artificial
<220> FEATURE:
<223> OTHER INFORMATION: Primer

<400> SEQUENCE: 3
agaagcagcg tcagtacccc t                                      21

<210> SEQ ID NO 4
<211> LENGTH: 20
<212> TYPE: DNA
<213> ORGANISM: Artificial
<220> FEATURE:
<223> OTHER INFORMATION: Primer

<400> SEQUENCE: 4
ctgcacggga ctcaagagac                                        20
```